US006117655A

United States Patent [19]

Capon et al.

[11] Patent Number: 6,117,655
[45] Date of Patent: *Sep. 12, 2000

[54] NUCLEIC ACID ENCODING ADHESION VARIANTS

[75] Inventors: Daniel J. Capon, San Mateo; Timothy J. Gregory, Hillsborough, both of Calif.

[73] Assignee: Genentech, Inc., South San Francisco, Calif.

[*] Notice: This patent is subject to a terminal disclaimer.

[21] Appl. No.: 08/457,918

[22] Filed: Jun. 1, 1995

Related U.S. Application Data

[63] Continuation of application No. 08/236,311, May 2, 1994, Pat. No. 5,565,335, which is a continuation of application No. 07/936,190, Aug. 26, 1992, Pat. No. 5,336,603, which is a division of application No. 07/842,777, Feb. 18, 1992, abandoned, which is a continuation of application No. 07/250,785, Sep. 28, 1988, abandoned, which is a continuation-in-part of application No. 07/104,329, Oct. 2, 1987, abandoned.

[51] Int. Cl.⁷ ............................ C12N 15/13; C12N 15/62; C12N 15/63

[52] U.S. Cl. ....................... 435/69.7; 536/23.1; 536/23.4; 536/23.5; 536/23.53; 435/71.1; 435/71.2; 435/325; 435/252.3; 435/254.11; 435/320.1; 435/471

[58] Field of Search ..................... 435/69.7, 71.1, 435/71.2, 325, 252.3, 254.11, 320.1, 471; 536/23.4, 23.1, 23.5, 23.53

[56] References Cited

U.S. PATENT DOCUMENTS

| | | | |
|---|---|---|---|
| 3,959,080 | 5/1976 | Orth et al. | 435/179 |
| 4,002,531 | 1/1977 | Royer | 435/188 |
| 4,055,635 | 10/1977 | Green et al. | 424/400 |
| 4,301,144 | 11/1981 | Iwashita | 514/6 |
| 4,412,989 | 11/1983 | Iwashita | 530/402 |
| 4,431,739 | 2/1984 | Riggs | 435/257.3 |
| 4,444,878 | 4/1984 | Paulus et al. | 435/7.1 |
| 4,745,055 | 5/1988 | Schenk | 435/7.6 |
| 4,761,371 | 8/1988 | Bell et al. | 435/69.1 |
| 4,766,106 | 8/1988 | Katre | 514/12 |
| 4,816,567 | 3/1989 | Cabilly et al. | 530/387 |
| 4,879,211 | 11/1989 | Wang et al. | 435/5 |
| 5,116,964 | 5/1992 | Capon et al. | 435/64.7 |

FOREIGN PATENT DOCUMENTS

| | | |
|---|---|---|
| 068763 | 1/1983 | European Pat. Off. . |
| 088695 | 9/1983 | European Pat. Off. . |
| 120694 | 10/1984 | European Pat. Off. . |
| 139416 | 5/1985 | European Pat. Off. . |
| 173494 | 3/1986 | European Pat. Off. . |
| 244221 | 11/1987 | European Pat. Off. . |
| 255694 | 2/1988 | European Pat. Off. . |
| 256654 | 2/1988 | European Pat. Off. . |
| 266663 | 5/1988 | European Pat. Off. . |
| 278776 | 8/1988 | European Pat. Off. . |
| 296786 | 12/1988 | European Pat. Off. . |
| 313377 | 4/1989 | European Pat. Off. . |
| 319815 | 6/1989 | European Pat. Off. . |
| 325262 | 7/1989 | European Pat. Off. . |
| 330227 | 8/1989 | European Pat. Off. . |
| 331356 | 9/1989 | European Pat. Off. . |
| WO 85/03947 | 9/1985 | WIPO . |
| WO 87/03600 | 6/1987 | WIPO . |
| WO 88/01304 | 2/1988 | WIPO . |
| WO 88/03559 | 5/1988 | WIPO . |
| WO 88/07376 | 10/1988 | WIPO . |
| WO 88/09344 | 12/1988 | WIPO . |
| WO 89/01940 | 3/1989 | WIPO . |
| WO 89/03221 | 4/1989 | WIPO . |

OTHER PUBLICATIONS

Miller et al., *Science* 244: 334–337, Apr. 21, 1989.
Blank et al, *Nature* 337: 187–189, Jan. 12, 1989.
Maddon et al., *Cell* 42: 93–104, Aug. 1985.
Treiger et al, *J. of Immunol.* 136(11): 4099–4105, Jun. 1, 1986.
Neuberger et al, *Nature* 312; 604–608, Dec. 13, 1987.
Gascoigne et al. "Secretion of a chimeric T–cell receptor–immunoglobulin protein". P.N.A.S. 84:2936–2940, May 1987.
Anderson et al., "Regulatory Interactions Between Members of the Immunoglobulin Superfamily" *Immunology Today* 9(7 & 8): 199–203 (1988).
Beauchamp et al., "A new procedure for the synthesis of polyethylene glycol–protein adducts; effects on function, receptor recognition, and clearance of superoxide dismutase, lactoferrin, and alpha 2–macroglobulin" *Analytical Biochemistry* 131(1): 25–33 (1983).
Blank et al., "Complete structure and expression in transfected cells of high affinity IgE receptor" *Nature* 337(6203): 187–189 (1989).
Boulianne, G. L. et al., "Production of functional chimaeric mouse/human antibody" *Nature* 312(5995): 643–646 (Dec. 1984).
Chaudhary et al., "Activity of a recombinant fusion protein between transforming growth factor type alpha and Pseudomonas toxin" *Proc. Natl. Acad. Sci. USA* 84:4538–4542 (1987).
Clark et al., "Peptide and nucleotide sequences for rat CD4 (W3/25) antigen: Evidence for derivation from a structure with four immunoglobulin–related domains" *Proc. Natl. Acad. Sci.* 84:1649–1653 (1987).

(List continued on next page.)

*Primary Examiner*—Prema Mertz
*Attorney, Agent, or Firm*—Jeffrey S. Kubinec

[57] ABSTRACT

Novel derivatives of cell surface proteins which are homologous to the immunoglobulin superfamily (adhesons) are provided. Amino acid sequence variations are introduced into adheson, the most noteworthy of which are those in which the transmembrane and, preferably, cytoplasmic domains are rendered functionally inactive, and in which adheson extracellular domains replace an immunoglobulin variable region. These variants are useful in therapy or diagnostics, in particular, CD4 variants are therapeutically useful in the treatment of HIV infections.

30 Claims, 13 Drawing Sheets

OTHER PUBLICATIONS

Estess et al., "Analysis of T–cell receptor structure and function using chimeric T–cell receptor/immunoglobulin molecules" *Journal of Cellular Biochemistry Supplement* 11(Part D, Abs. 331):258 (1987).

Falkner and Zachau, "Expression of mouse immunoglobulin genes in monkey cells" *Nature* 298:286–288 (1982).

Gascoigne et al., "Secretion of a chimeric T cell receptor–immunoglobulin protein" *Proc. Natl. Acad. Sci. USA* 84:2936–2940 (1987).

Gascoigne et al., "Secretion of chimeric T–cell receptor–immunoglobulin fusion proteins" *Journal of Cellular Biochemistry Supplement* 11(Part D, Abs. 333):259 (1987).

Goverman et al., "Chimeric T–cell receptor genes as tools in analyzing T–cell/target–cell interactions" *Journal of Cellular Biochemistry Supplement* 11(Part D, Abs. 334):259 (1987).

Hashimoto et al., "Rearrangement and expression of T cell receptor genes in pre–T cells" *Journal of Cellular Biochemistry Supplement* 11(Part D, Abs. 434):278 (1987).

Ivars et al., "Expression of cloned T cell receptor genes" *Journal of Cellular Biochemistry Supplement* 11(Part D, Abs. 435):278 (1987).

Johnson et al., "Correlation of T cell receptor structure and function" *Journal of Cellular Biochemistry Supplement* 11(Part D, Abs. 337):260 (1987).

Kohler, G., "Immunoglobulin chain loss in hybridoma lines" *Proc. Natl. Acad. Sci. USA* 77(4):2197–2199 (1980).

Littman DR, "The isolation and sequence of the gene encoding T8: a molecule defining functional classes of T lymphocytes" *Cell* 40(2):237–246 (1985).

Littman DR, "The structure of the CD4 and CD8 genes" *Annual Review of Immunology* 5:561–584 (1987).

Maddon et al., "The Isolation and Nucleotide Sequence of a cDNA Encoding the T Cell Surface Protein T4: A New Member of the Immunoglobulin Gene Family" *Cell* 42:93–104 (1985).

Maddon et al., "The T4 Gene Encodes the AIDS Virus Receptor and Is Expressed in the Immune System and the Brain" *Cell* 47:333–348 (1986).

Maddon P. et al., "Structure and expression of the human and mouse T4 genes" *Proc. Natl. Acad. Sci. USA* 84(24):9155–9159 (1987).

McDougal et al., "Binding of HTLV–III/LAV to T4+ Cells by a Complex of the 110k Viral Protein and the T4 Molecule" *Science* 231:382–385 (1986).

McDougal et al., "The T4 Glycoprotein Is a Cell–Surface Receptor for the AIDS Virus" *Molecular Biology of Homosapiens* (Cold Spring Harbor Symposia on Quantitative Biology), New York:CSHL vol. LI (1986).

Miller, Larry et al., "Expression of high–affinity binding of human immunoglobulin E by transfected cells" *Science* 244:334–336 (1989).

Morrison, "Transfectomas Provide Novel Chimeric Antibodies" *Science* 229:1202–1207 (1985).

Morrison and Oi, "Transfer and expression of immunoglobulin genes" *Annual Review of Immunology* 2:239–256 (1984).

Morrison, J., "Sequentially derived mutants of the constant region of the heavy chain of murine immunoglobulins" *J. of Immunology* 123(2):793–800 (1979).

Morrison, S. L. et al., "Chimeric human antibody molecules: mouse antigen–binding domains with human constant region domains" *Proc. Natl. Acad. Sci. USA* 81(21):6851–6855 (Nov. 1984).

Murre et al., "Biochemical and functional analyses of a secreted H–2L$^d$ molecule" *Molecular & Cellular Biology* 6:1315–1319 (1986).

Neuberger et al., "Recombinant antibodies possessing novel effector functions" *Nature* 312(5995):604–608 (Dec. 1984).

Oi, V.T. et al., "Chimeric Antibodies" *BioTechniques* 4(3):214–221 (1986).

Osborn, L. et al., "Direct expression cloning of vascular cell adhesion molecule 1, a cytokine–induced endothelial protein that binds to lymphocytes" *Cell* 59:1203–1211 (1989).

Peterson, A.S., "Genetic analysis of CD2/LFA–3 and CD4/HIV interactions" (thesis), Harvard University, Chapter 1, (1988).

Rose and Bergmann, "Expression from Cloned cDNA of Cell–Surface Secreted Forms of the Glycoprotein of Vesicular Stomatitis Virus in Eucaryotic Cells" *Cell* 30:753–762 (1982).

Rosenblum et al., "Modification of human leukocyte interferon pharmacology with a monclonal antibody" *Cancer Research* 45:2421–2424 (1985).

Salzawa et al., "The CD4 molecule is associated with the T–cell receptor" *Journal of Cellular Biochemistry Supplement* 11(Part D, Abs. 421):273 (1987).

Seed B., "An LFA–3 cDNA encodes a phospholipid–linked membrane protein homologous to its receptor CD2" *Nature* 329:840–842 (1987).

Sharon et al., "Expression of a $V_h C_k$ Chimaeric Protein in Mouse Myeloma Cells" *Nature* 309:364–367 (1984).

Sleckman et al., "Expression and function of CD4 in a murine T–cell hybridoma" *Nature* 328(6128):351–353 (1987).

Smith et al., "Blocking of HIV–1 Infectivity by a Soluble, Secreted Form of the CD4 Antigen" *Science* 238:1704–1707 (1987).

Springer and Strominger, "Detergent–soluble HLA antigens contain a hydrophilic region at the COOH–terminus and a penultimate hydrophobic region" *Proc. Natl. Acad. Sci. USA* 73(7):2481–2485 (1976).

Terhorst C. et al., "Biochemical analysis of human T lymphocyte differentiation antigens T4 and T5" *Science* 209(4455):520–521 (1980).

Traunecker et al., "Highly efficient neutralization of HIV with recombinant CD4–immunoglobulin molecules" *Nature* 339:68–70 (1989).

Traunecker et al., "Soluble CD4 molecules neutralize human immunodeficiency virus" *Nature* 331:84–86 (1988).

Vitetta et al., "Redesigning nature's poisons to create anti-–tumor reagents" *Science* 238:1098–1104 (1987).

Wills et al., "Mutations of the Rous Sarcoma Virus env Gene that affect the transport and subcellular location of the glycoprotein products" *Journal of Cell Biology* 99:2011–2023 (1984).

```
                bstXI                                                                         mnlI
          aluI                                                                         mnlI   haeIII
     sacI bstNI           scrFI                                                  aluI   stuI
     hgiAI                bstNI                                                    nheI   haeI
     bsp1286       nlaIV                                   mboII
     banII   banI   nlaIII
601  GGAGCTCCAGGATAGTGGCACCTGGACATGCTCACTGTCTTGCAGAACCAGAAGAAGGTGGAGTTCAAAATAGACATCGTGGTGCTAGCTTTCCAGAAGGCC
     CCTCGAGTCCTATCACCGTGGACCTGTACGAGTGACAGAACGTCTTGGTCTTCTTCCACCTCAAGTTTTATCGTAGCACCACGATCGAAAGGTCTTCCGG
150  GluLeuGlnAspSerGlyThrTrpThrCysThrValLeuGlnAsnGlnLysLysValGluPheLysIleAspIleValLeuAlaPheGlnLysAla
                                         mnlI                        aluI                    aluI
701  TCCAGCATATAGTCTATATAAGAAAGAGGGGAACAGGTGGAGTTCTCCTTCCCACTCGCCTTTACAGTTGAAAAGTCGACGGGCAGTGGCGAGCTGTGTGGC
     AGGTCGTATATCAGATATATTCTTTCTCCCCCTTGTCCACCTCAAGAGGAAGGGTGAGCGGAAAATGTCAACTTTTCAGCTGCCCGTCACCGCTCGACACCACCG
183  SerSerIleValTyrLysLysValGluGlyGluGlnValGluPheSerPheProLeuAlaPheThrValGluLysSerThrGlySerGlyGluLeuTrpGln
                                        hphI                                   sau96I
                                        sau3AI                                   nlaIV
                                        dpnI                                     avaII
                         mnlI  pflMI  alwI                                       ppuMI
                mnlI  mnlI                                                 bstEII ecoO  ddeI  aluI
                                                                                bstNI
801  AGGCGGAGAGGGCTTCCTCCTCCAAGTCTTGGATCACCTTTGACCTGAAGAACAAGGAAGTGTCTGTAAAACGGGTTACCCAGGACCCTAAGCTCCAGAT
     TCCGCCTCTCCCGAAGGAGGAGGTTCAGAACTGGAAACTGGAAACTAGTAGGGAAACTAGATCAAAGACATTTGCCCAATGGGTCCTGGGATTCGAGTCTA
217  AlaGluArgAlaSerSerSerLysSerTrpIleThrPheAspLeuLysAsnLysGluValSerValLysArgValThrGlnAspProLysLeuGlnMet
```

FIG. 1B-2

```
                              sau96I
                              avaII
                              ppuMI
                              ecoO                                   sau96I
         avaI  alwNI          hinfI              nlaIII  avaI  alu1   mseI
         avaI                                       avaII  avaI  mseI
1201     CTCGGACAGTCCTGCTGGAATCCAACATCCAAGGTTCTGCCCACATGGTCCACCCCGAGCTTTAATGCGGTAGTTTATCACAGTTAAATTGCTAACGCA
         GAGCCTGTCCAGGACGACCTTAGGTTGTAGGTTGTAGTTCCAAGACGGGTGTACCAGGTGGGGCTCGAAATTACGCCATCAAATAGTGTCAATTTAACGATTGCGT
350      SerGlyGlnValLeuLeuGluSerAsnIleLysValLeuProTrpSerThrProSerPheAsnAlaValValTyrHisSerOC* sfaNI          scrFI
                                                  hinPI                      scrFI                 rsaI   nciI
              nlaIV                               hhaI    mnlI      nlaIV    bstNI                 mspI   mspI
              banI                                        fokI  banI hphI  fokI                    hpaII  hpaII
1301    GTCAGGCACCGTGTATGAAATCTAACAATGCGCTCATCGTCATCCCTCGGCACCCTGGATGCTGTAGGAGCAGTAGCCCGTGGTTATGCCGGTACTGCC
         CAGTCCGTGGCACATACTTTAGATTGTTACGCGAGTAGCAGTAGGGAGCCTGTGGGACCTACGACATCCGTCACATCCGCTCATCCGTACGAATACGGCCATGACGG mnlI
         haeIII
         sau96I
1401     GGGCCTCTTGCGGGAT
         CCCGGAGAACGCCCTA
```

```
                                                                                   scrFI
              thaI                                      mspI                       bstNI
     aluI  hinPI            sau3AI       mseI           hpaII             fnu4HI         nlaIV
     hindIII hhaI           dpnI         aflII
  1  AAGCTTCAGCGCGAACGACCAACTACCCCGATCATCAGTTATCTCTTTGTCTGTGCGTTCCGGTATGGGGGACTGCCGCCAGTTGG
     TTCGAAGTCGCGCTTGCTGGTTGATGGGGCTAGTAGTCAATAGAATTCCAGAGAAACACACGCAAGGCCATACCCCCTGACGGCGGTCCAACC
  1                                                              MetGlyThrAlaAlaArgLeuGly styI   thaI
                                  ncoI   sau96I                    haeIII            taqI
              haeIII            mnlI     avaII              sfaNI  eaeI              claI
              sau96I         haeIII    nlaIV  fnu4HI        foki  mnlI
 101 GGGCCGTGATTTGTTGTCGTCATAGTGGGCCTCCGCGGATGGGTCCGGCAAATATGCCTTGGCGGATGCCTCTCAAGATGCCGACCCCAATGATT
     CCCGGCACTAAAACAACAGCAGTATCACCCGGAGGCGCCTACCCAGGCGCCGTTTATACGGAACGCCTACGAGAGTTCTACCGCTGGGTTAGCTAA
  10           AlaValIleLeuPheValValIleValGlyValArgGlyLeuHisGlyValArgGlyLeuLysTyrAlaLeuAlaAspProAsnArgPhe scrFI   fnu4HI
                           sau96I  aluI                                                  aluI
                      avaII sau96I xhoI                                                  rsaI
              fnu4HI   mspI bstNI  pvuII avaI
              thaI     hpaII   avaII bbvI taqI                                                alu1
 201 TCGCGGCAAAGACCTTCCGGTCCTGGACCTGCTCGAGCAGGAGAACAAAGGGGATACAGTGGAACTGACCTGTACAGCT
     AGCGCCGTTTCTGGAAGGCCAGGACCTGGACGAGCTCGTCCTCTTGTTTCCCTATGTCACCTTGACTGGACATGTCGA
  43  ArgGlyLysAspLeuProValLeuAspLeuLeuGluGlnGluLeuLeuLysValValLeuGlyLysValLysGlyLysAspThrValThrAla fokI
                                                                               sau96I
                                                             nlaIV             avaII    aluI
                                                             bsp1286
              mboII                               hinfI      banII    mseI     alwNI    aluI
              mboII
 301 TCCCAGAAGAAGAGCATACAATTCCACTGGAAAAACTCCAACCAGATAAAGATTCTGGGAAATCAGGGCTCCTTCTTAACTAAAGGTCCATCCAAGCTGA
     AGGGTCTTCTTCTCGTATGTTAAGGTGACCTTTTGAGGTTGGTCTATTTCTAAGACCCTTTAGTCCCGAGGAAGAATTGATTCCAGTTAGGTTCGACT
  76 SerGlnLysLysSerIleGlnPheHisTrpLysAsnSerAsnGlnIleLeuSerIleLeuGlyAsnGlnGlySerPheLeuThrLysGlyProSerLysLeuAsn ddeI
             hinPI                                                  pleI
             hhaI            styI                                   hinfI
             thaI            sau96I          sau3AI       mseI
             sau3AI  pleI    avaII           dpnI         aflIII
             dpnI    hinfI   mboII           nlaIV        hinfI     mboII
 401 ATGATCGCGCTGACTCAAGAAGAAGCCTTTGGACCAAGGAAACTTTCCCCTGATCATCAAGAATTCTTAAGATAGAACTCAGATACTTACATCTGTGA
     TACTAGCGCGACTGAGTTCTTCTTCGGAAACCTGGTTCCTTTGAAAGGGACTAGTAGTTCTTAGAATTCTATCTTGAGTCTATGAATGTAGACACT
 110   AspArgAlaAspSerArgArgSerLeuTrpAspGlnPheProLeuIleLeuIleLysAsnLeuLysIleLeuGluAspSerAspThrTyrIleCysGlu ecoNI            styI
              sau96I                                                      bspMI          alwNI
              avaII                                                                        styI
              mnlI           mnlI
 501 AGTGGAGGACCAGAGGAGGAGTGCAATTGCTAGTGTTCGGATTGACTGCAACTGCCACACCCTGACCACCTGCTTCAGGGGCAGAGCCTCAGCCCTGACCCTTG
     TCACTCCTGGTCTCCTCCTCACGTTAACGATCACAAGCCTAACTGACGTTGACGTGGGTGGTGGACTGGTGGACGAAGTCCCCGTCTCCGGAGTCGGGAAC
 143 ValGluAspGlnLysGluGluValGlnLeuLeuValPheGlyLeuThrAlaAsnSerAspThrHisLeuLeuGlyGlnSerLeuThrLeuThrLeu
```

FIG. 2B-1

```
                                                                                                       scrFI
                                                                                                       bstXI
                                                                                             aluI
                                                                                             sacI bstNI
                                                                             aluI hgiAI
                                                                             pvuII bsp1286
                                                                  mboII mnlI      ddeI banII
      scrFI                      styI
      bsp1286     ddeI           pleI
      banII bstNI      mnlI      hinfI
601 GAGAGCCCCCTGGTAGTAGCCAGTGCAATGTAGGAGTCCAAGGGGTAAAAACATACAGGGGGGAAGACCCTCCGTGTCTCAGCTGGAGCTCC
    CTCTCGGGGGACCATCATCGGTCACGTTACATCCTCAGGTTCCCCATTTTTGTATGTCCCCCCCTTCTGGAGAGGCACAGAGTCGACCTCGAGG
176 GluSerProProGlySerProSerValGlnCysSerProArgGlyLysAsnIleGlnGlyLysThrLeuSerValSerGlnLeuGluLeuGln mnlI
      scrFI                                                                               haeIII
      bstNI                                                                   aluI        stuI
           nlaIV                                                              nheI        haeI
           banI          nlaIII              mboII
701 AGGATAGTGCACCTGGACCTGCACTGTCTTGCAGAACCAGAAGAAGGTGGAGTTCAAAATAGACATCGTGGTGCTAGCTTTCAGAAGGCCTCCAGCAT
    TCCTATCACGTGGACCTGGACGTGACAGAACGTCTTGGTCTTCTTCCAAGTTTTATCTGTAGCACCACGATCGAAAGGTCTTCCGGAGGTCGTA
210 AspSerGlyThrTrpThrCysThrValLeuGlnAsnGlnLysLysValGluPheLysIleAspIleValValLeuAlaPheGlnLysAlaSerSerIle mnlI
      mnlI                                                 aluI                  aluI
801 AGTCTATAAGAAGAGGGGAACAGTGGAGTTCTCCTCCCACTCGCTTTACAGTTGAAAAGTCGACGGGCAGTGGCGAGCTGGCCAGTGGTGCAGGCGGAG
    TCAGATATTCTTCTCCCCTTGTCCACCTCAAGAGGAGGGTGAGCGAAATGTCAACTTTTCAGCTGCCCGTCGACCGCTGACCACCGTCCGCCTC
243 ValTyrLysLysGluGlyGluGlnValGluPheSerProLeuAlaPheThrValGluLysSerAspGlyGlnTrpGlnAlaGlu sau96I
                                                                     nlaIV
      hphI                                                           avaII
      sau3AI                                                         ppuMI
      dpnI                                                           scrFI
      mnlI pflMI   alwI                                              bstNI  ecoO  ddeI      aluI
                                 mboII                               bstEII
901 AGGGCTTCCTCTCCCAAGTCTCTTGGATCACCTTTGACCTGAAGAACAAGGAAGTGTCTGTAAAACGGGTTACCACCTAAGCTCCAGATGGGCAAGA
    TCCCGAAGGAGAGGGTTCAGAGAACCTAGTGGAAACTGGACTTCTTGTTCCTTCACAGACATTTGCCAATGGGTCCTGGATTCGAGGTCTACCCGTTCT
276 ArgAlaSerSerLysSerTrpIleThrPheAspLeuLeuAsnLysGluValSerValLysArgValThrGlnAspProLysLeuMetGlyLysLysLys
```

Immunoglobulin $\gamma_1$

Soluble rCD4

$CD4_2\gamma_1$ $CD4_4\gamma_1$

FIG. 4A

```
                                                            rsaI        hgaI                              taqI    sau96I
          thaI    haeIII                                                                                sau3AI   nlaIV
          sacII   xmaII                                                                                 dpnI     ecoO
    ecoRI fnu4HI  eaeI                                                                                  alwI     scrFI
  1 GAATTCTGTCACTGCCGCGGACAGGCCGGCCTATATTACTGCGAGAGCCACCTTTGCCTATGGTACAGGAGCGTCCCCCTTGTTGATGACCCCTGG    bstNI
    CTTAAGACAGTGACGGCGCCTGTCCGGCCGGCATATAATGACACGCTTCGGTGGAAAACGATACCATGTCCTCGCAGGGGGAACAACCTAGCTGGGACC
 72     ValThrAlaAlaAspThrAlaValTyrTyrCysAlaAlaThrPheCysLeuTrpTyrArgAlaArgProProCysTrpIleAspProTrp
                                                        sau96I
                                                        sau96I
                                                        nlaIV
                                                        bsp1286
                                                        banII               nlaIV
                                                        apaI                banI
      nlaIV    hphI                                     ecoO                scrFI       mnlI  hgiAI           sau96I
      scrFI    bstEII                                                       bstNI             bsp1286         fnu4HI
      bstNI    scrFI           mnlI mnlI styI haeIII    mboII               hhaI              bsp1286 haeIII
      haeIII   bstNI                                                                                  
101 GGCCTGGGAACCCTGGTCACCGTCTCCTCGGCCTCCACCAAGGGCCCATCGGTCTTCCCCCTGGCACCCTCCTCCAAGAGCACCTCTGGGGGCACAGCGG
    CCGGACCCTTGGGACCAGTGGCAGAGGAGCCGGAGGTGGTTCCCGGGTAGCCAGAAGGGGGACCGTGGGAGGAGGTTCTCGTGGAGACCCCCGTGTCGCC
103   GlyLeuGlyThrLeuValThrValSerSerAlaSerThrLysGlyProSerValPheProLeuAlaProSerSerLysSerThrSerGlyGlyThrAlaAla
                                                              hinPI
                                                              nlaIV
                                                              narI
                                                              haeII              hgiAI    mspI
                                                              banI               bsp1286  hpaII
          scrFI                                        scrFI  ahaII              apaLI    scrFI
          fnu4HI       hphI                            fnu4HI ddeI hhaI                   ncII
          bbvI         mspI tth111I
201 CCCTGGGCTGCCTGGTCAAGGACTACTTCCCCGAACTGGTGACGGTGTCGTGGAACTCAGGCGCCCTGACCAGCGGCGTGCACACCTTCCCGGCTGTCCT
    GGGACCCGACGGACCAGTTCCTGATGAAGGGCTTGACCACTGCCACAGCACCTTGAGTCCGCGGGACTGGTCGCCGCACGTGTGGAAGGGCCGACAGGA
137   LeuGlyCysLeuValLysAspTyrPheProGluValThrValSerTrpAsnSerGlyAlaLeuThrSerGlyValHisThrPheProAlaValLeu
              ddeI                                          alul
              mstII pleI                                    bstXI nlaIV
              mnlI hinfI              ddeI        fnu4HI          banI
              eco81I       mnlI  bbvI hphI  bstEII bsp1286   bbvI bsp1286                 hinfI
301 ACAGTCCTCAGGACTCTACTCCCTCAGCAGCTGCCCTCCAGCAGCTTGGGACCCAGACTCACATCTGCAACGTGAATCACAAGCCCAGC
    TGTCAGGAGTCCTGAGATGAGGAGTCGTCGACGGGAGGTCGTCGAACCCTGGTCTGAGTAGACGTTGCACTTAGTGTTCGGGTCG
170   GlnSerSerGlyLeuTyrSerLeuSerSerValValThrValProSerSerSerLeuGlyThrGlnThrTyrIleCysAsnValAsnHisLysProSer
                                                                                                                sau96I
              bsp1286                                       alwNI                                         scrFI  avaII
              banII                              nlaIII     bsp1286                                       bstNI  nlaIV mboII
401 AACACCAAGGTGGACAAGAAAGTTGAGCCCAAAATCTTGTGACAAATCTCACACATGCCCACCGTGCCCAGCACCTGAACTCCTGGGGGACCGTCAGTCT
    TTGTGGTTCCACCTGTTCTTTCAACTCGGGTTTTAGAACACTGTTTAGAGTGTGTACGGGTGGCACGGGTCGTGGACTTGAGGACCCCCTGGCAGTCAGA
203   AsnThrLysValAspLysLysValGluProLysSerCysAspLysThrHisThrCysProProCysProAlaProGluLeuLeuGlyGlyProSerValPhe
                                       ↑
                                       Fc
```

NUCLEIC ACID ENCODING ADHESION VARIANTS

This application is a continuation of U.S. Ser. No. 08/236,311 filed May 2, 1994 now U.S. Pat. No. 5,565,335, which is a continuation of U.S. Ser. No. 07/936,190 filed Aug. 26, 1992, now U.S. Pat. No. 5,336,603, which is a divisional of 07/842,777 filed Feb. 18, 1992, now abandoned, which is a continuation of U.S. Ser. No. 07/250,785 filed Sep. 28, 1988, now abandoned, which is a continuation-in-part of U.S. Ser. No. 07/104,329 filed Oct. 2, 1987, now abandoned.

BACKGROUND OF THE INVENTION

This application relates to compositions for antiviral or immunomodulatory therapy. In particular, it relates to compositions useful in the treatment of Human Immunodeficiency Virus (HIV) infections.

The primary immunologic abnormality resulting from infection by HIV is the progressive depletion and functional impairment of T lymphocytes expressing the CD4 cell surface glycoprotein (H. Lane et al., Ann. Rev. Immunol. 3:477 [1985]). CD4 is a non-polymorphic glycoprotein with homology to the immunoglobulin gene superfamily (P. Maddon et al., Cell 42:93 [1985]). Together with the CD8 surface antigen, CD4 defines two distinct subsets of mature peripheral T cells (E. Reinherz et al., Cell 19:821 [1980]), which are distinguished by their ability to interact with nominal antigen targets in the context of class I and class II major histocompatibility complex (MHC) antigens, respectively (S. Swain, Proc. Natl. Acad. Sci. 78:7101 [1981]; E. Engleman et al., J. Immunol. 127:2124 [1981]; H. Spitz et al., J. Immunol. 129:1563 [1982]; W. Biddison et al., J. Exp. Med. 156:1065 [1982]; and D. Wilde et al., J. Immunol. 131:2178 [1983]). For the most part, CD4 T cells display the helper/inducer T cell phenotype (E. Reinherz, supra), although CD4 T cells characterized as cytotoxic/suppressor T cells have also been identified (Y. Thomas et al., J. Exp. Med. 154:459 [1981]; S. Meuer et al., Proc. Natl. Acad. Sci. USA 79:4395 [1982]; and A. Krensky et al., Proc. Natl. Acad. Sci. USA 79:2365 [1982]). The loss of CD4 helper/inducer T cell function probably underlies the profound defects in cellular and humoral immunity leading to the opportunistic infections and malignancies characteristic of the acquired immunodeficiency syndrome (AIDS) (H. Lane supra).

Studies of HIV-I infection of fractionated CD4 and CD8 T cells from normal donors and AIDS patients have revealed that depletion of CD4 T cells results from the ability of HIV-I to selectively infect, replicate in, and ultimately destroy this T lymphocyte subset (D. Klatzmann et al., Science 225:59 [1984]). The possibility that CD4 itself is an essential component of the cellular receptor for HIV-I was first indicated by the observation that monoclonal antibodies directed against CD4 block HIV-I infection and syncytia induction (A. Dalgleish et al., Nature [London] 312:767 [1984]; J. McDougal et al., J. Immunol. 135:3151 [1985]). This hypothesis has been confirmed by the demonstration that a molecular complex forms between CD4 and gp120, the major envelope glycoprotein of HIV-I (J. McDougal et al., Science 231:382 [1986]); and the finding that HIV-I tropism can be conferred upon ordinarily non-permissive human cells following the stable expression of a CD4 cDNA (P. Maddon et al., Cell 47:333 [1986]). Furthermore, the neurotropic properties of HIV-I, reflected by a high incidence of central nervous system dysfunction in HIV-I infected individuals (W. Snider et al., Ann. Neurol. 14:403 [1983]), and the ability to detect HIV-I in the brain tissue and cerebrospinal fluid of AIDS patients (G. Shaw et al., Science 227:177 [1985]; L. Epstein, AIDS Res. 1:447 [1985]; S. Koenig, Science 233:1089 [1986]; D. Ho et al., N. Engl. J. Med. 313:1498 [1985]; J. Levy et al., Lancet II:586 [1985]), appears to be explained by the expression of CD4 in cells of neuronal, glial and monocyte/macrophage origin (P. Maddon, Cell 47:444 [1986]; I. Funke et al., J. Exp. Med. 165:1230 [1986]; B. Tourvieille et al., Science 234:610 [1986]).

In addition to determining the susceptibility to HIV-I infection, the manifestation of cytopathic effects in the infected host cell appears to involve CD4. Antibody to CD4 was found to inhibit the fusion of uninfected CD4 T cells with HIV-I infected cells in vitro; moreover, the giant multinucleated cells produced by this event die shortly after being formed, resulting in the depletion of the population of CD4 cells (J. Lifson et al., Science 232:1123 [1986]). Formation of syncytia also requires gp120 expression, and can be elicited by coculturing CD4-positive cell lines with cell lines expressing the HIV-I env gene in the absence of other viral structural or regulatory proteins (J. Sodroski et al., Nature 322:470 [1986]; J. Lifson et al., Nature 323:725 [1986]). Thus, in mediating both the initial infection by HIV-I as well as eventual cell death, the interaction between gp120 and CD4 constitutes one of several critical entry points in the viral life cycle amenable to therapeutic intervention (H. Mitsuya et al., Nature 325:773 [1987]).

The known sequence of the CD4 precursor predicts a hydrophobic signal peptide, an extracellular region of approximately 370 amino acids, a highly hydrophobic stretch with significant identity to the membrane-spanning domain of the class II MHC beta chain, and a highly charged intracellular sequence of 40 residues (P. Madden, Cell 42:93 [1985]). The extracellular domain of CD4 consists of four contiguous regions each having amino acid and structural similarity to the variable and joining (V-J) domains of immunoglobulin light chains as well as related regions in other members of the immunoglobulin gene superfamily (a subclass of which are defined herein by the coined term "adhesons". These structurally similar regions of CD4 are termed the $V_1$, $V_2$, $V_3$ and $V_4$ domains (denominated 1–4 in FIG. 3).

A successful strategy in the development of drugs for the treatment of many receptor mediated abnormalities has been the identification of antagonists which block binding of the natural ligand. Since the CD4 adheson ordinarily binds to the recognition sites of the HIV envelope it would appear to be a candidate for therapeutically sequestering these HIV sites, thereby blocking viral infectivity. However, full length CD4 and other adhesons are cell membrane proteins which are anchored in the lipid bilayer of cells. The presence of membrane components will be undesirable from the standpoint of manufacturing and purification. In addition, since adhesons are normally present only on cell surfaces, it would be desirable to produce adhesons in a form which is more stable in the circulation. Additionally, even truncated, soluble CD4 adheson (generally referred to as CD4T) may not be optimally effective as a therapeutic since it possesses a relatively short biological half-life, binds to HIV no better than cell surface CD4, may not cross the placental or other biological barriers, and merely sequesters the HIV recognition sites without in itself bearing an infected-cell killing or virus killing functionality.

Accordingly, it is an object of this invention to produce soluble, secreted adhesons. It is another object to produce CD4 derivatives useful in the treatment of AIDS and related conditions, in a manner essentially unaffected by the extreme degree of genetic variation observed among various HIV-I isolates and their respective env polypeptides (J. Coffin, Cell 46:1 [1986]). Still another object is to prepare adhesons fused to other polypeptides in order to provide molecules with novel functionalities such as those described above for therapeutic use, or diagnostic reagents for the in vitro assay of adhesons or their ligands. In particular, it is an objective to prepare molecules for directing toxins or effector molecules (for example the Fc domain of immunoglobulin) to cells bearing receptors for the adhesons, e.g. HIV gp120 in the case of CD4, and for use in facilitating purification of the adhesons. It is a further object to provide stable, highly purified adheson preparations.

SUMMARY

The objects of this invention are accomplished by providing nucleic acid encoding an amino acid sequence variant of an adheson, in particular a variant in which the transmembrane domain is modified so that it is no longer capable of becoming lodged in the cell membrane. In the case of CD4 such variants are termed soluble CD4.

Variant adhesons are produced by a method comprising (a) transforming a host cell with nucleic acid encoding an amino acid sequence variant of an adheson, (b) culturing the host cell and (c) recovering the variant adheson from the host cell culture media or from lysates of the host cell.

In specific embodiments, the objects of this invention are accomplished by providing an adheson variant selected from the group consisting of (a) an adheson amino acid sequence variant having an inactivated transmembrane domain and (b) a polypeptide comprising an adheson extracellular domain fused to the sequence of a polypeptide which is different from the adheson, this latter, for example, selected from a cytotoxin, an immunogen or a protein with a long plasma half life such as an immunoglobulin constant domain.

In a preferred embodiment a polypeptide comprising a gp120 binding domain of the CD4 adheson is fused at its C-terminus to an immunoglobulin constant domain, or is linked to a cytotoxic polypeptide such as ricin.

The CD4 adheson variants provided herein are purified and formulated in pharmacologically acceptable vehicles for administration to patients in need of antiviral, neuromodulatory or immunomodulatory therapy, in particular patients infected with HIV, and for use in the modulation of cell adhesion.

BRIEF DESCRIPTION OF THE DRAWINGS

Figure 1B-2:
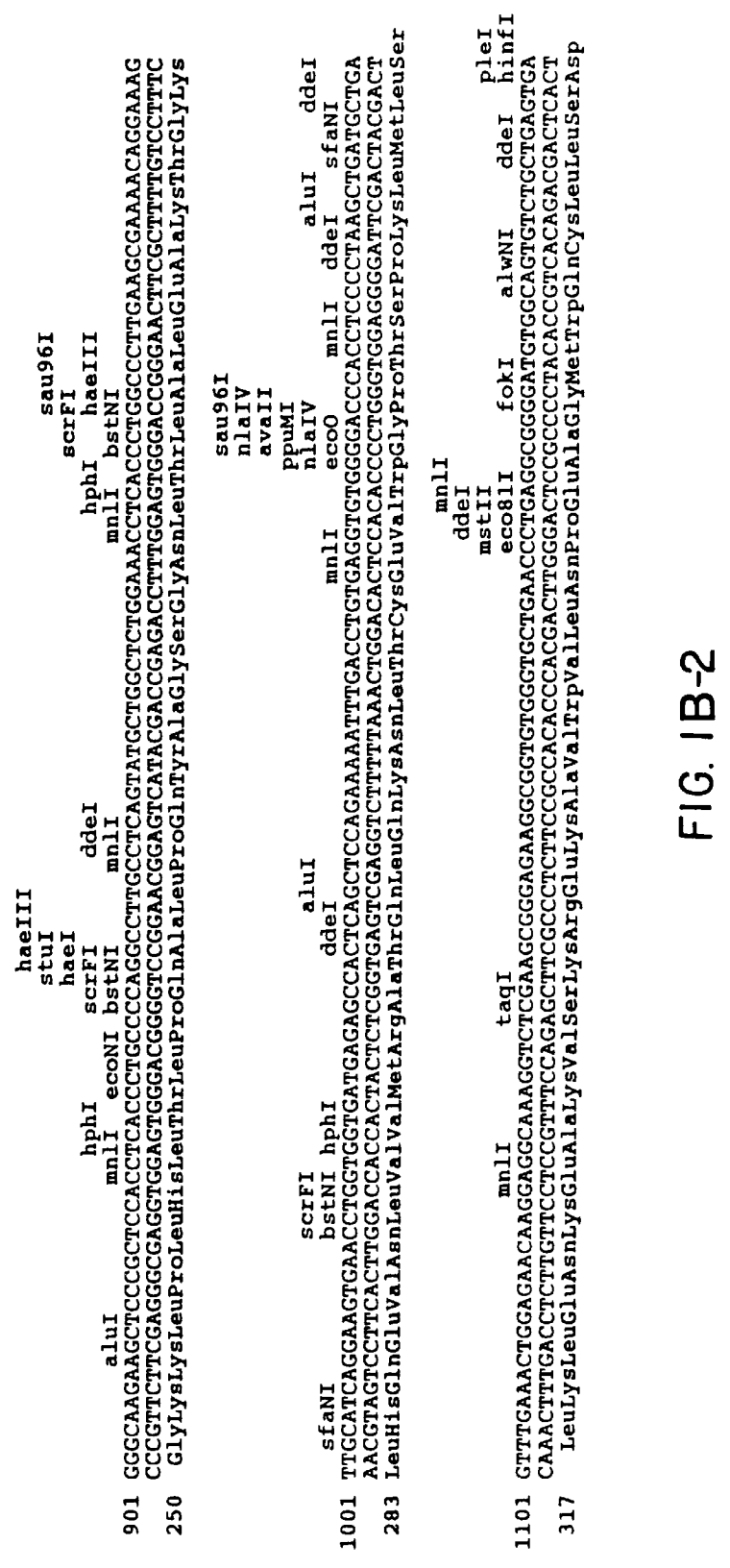
Figure 2B-2:
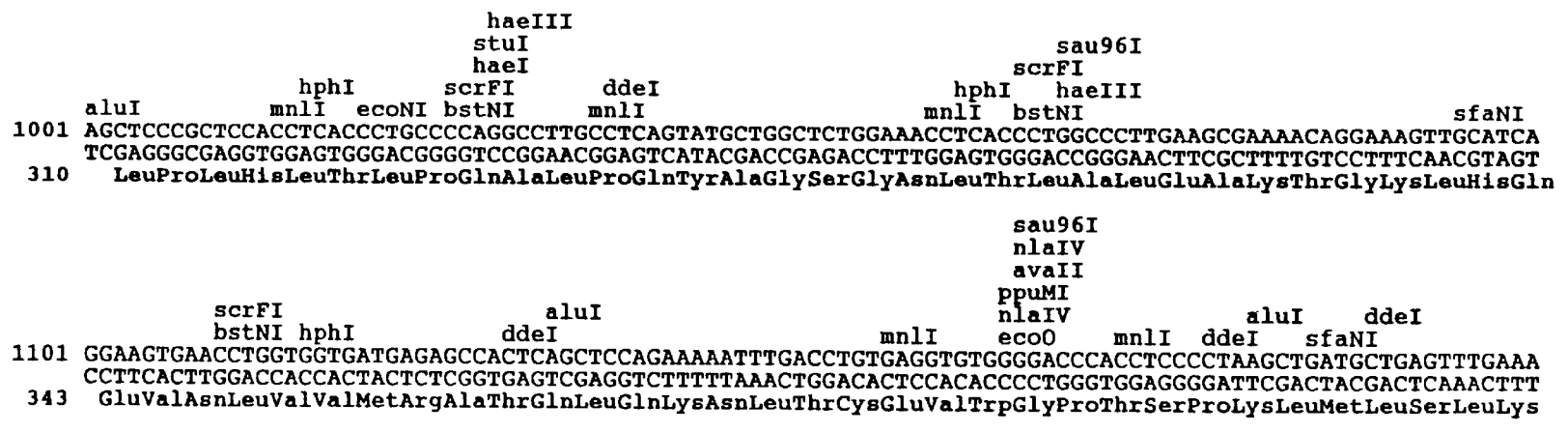
Figure 2C:
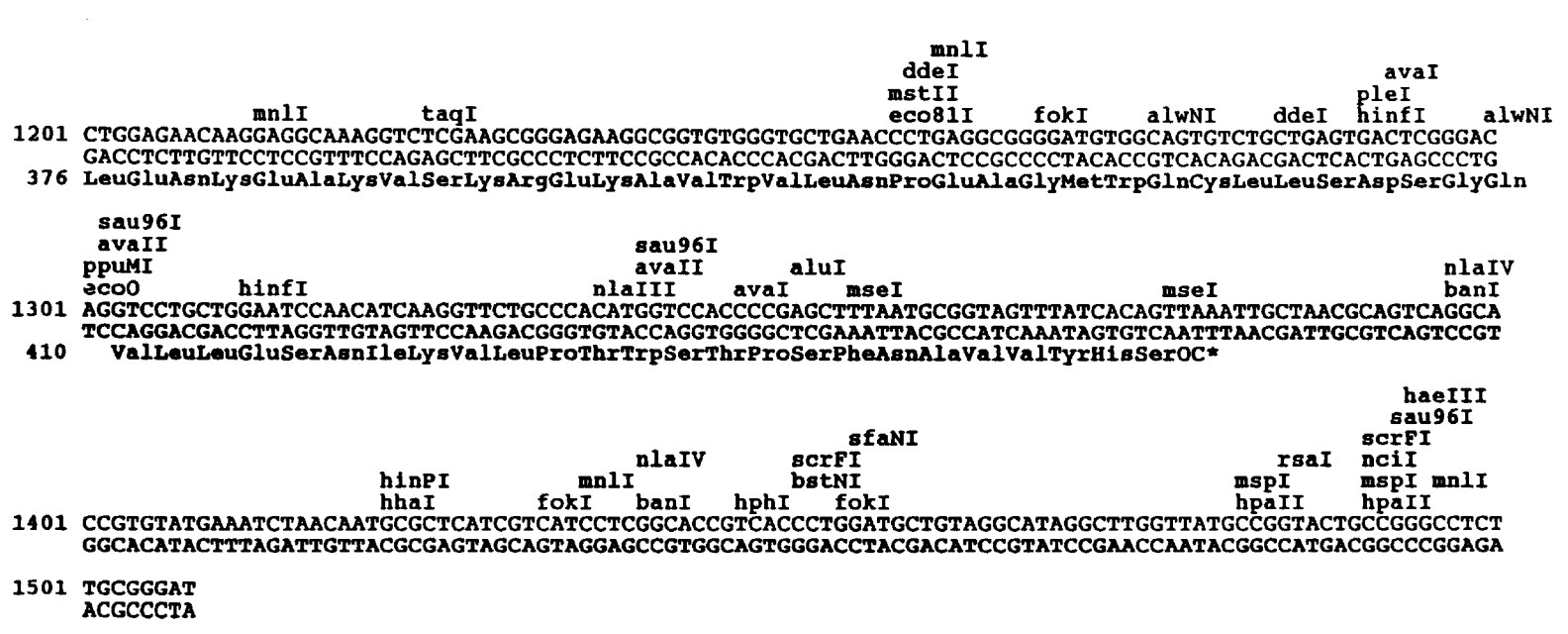

FIGS. 1A, 1B-1, 1B-2, and 1C depict the amino acid and nucleotide sequences (SEQ ID NOS:1–3, respectively) of a secreted form of the CD4 adheson. The signal processing site is designated with an arrow.

FIGS. 2A, 2B-1, 2B-2, and 2C depict the amino acid and nucleotide sequences (SEQ ID NOS:4–6, respectively) of a fusion of the herpes gD leader and N-terminal 27 residues to the putative mature N-terminus of CD4T.

Figure 4B-1:
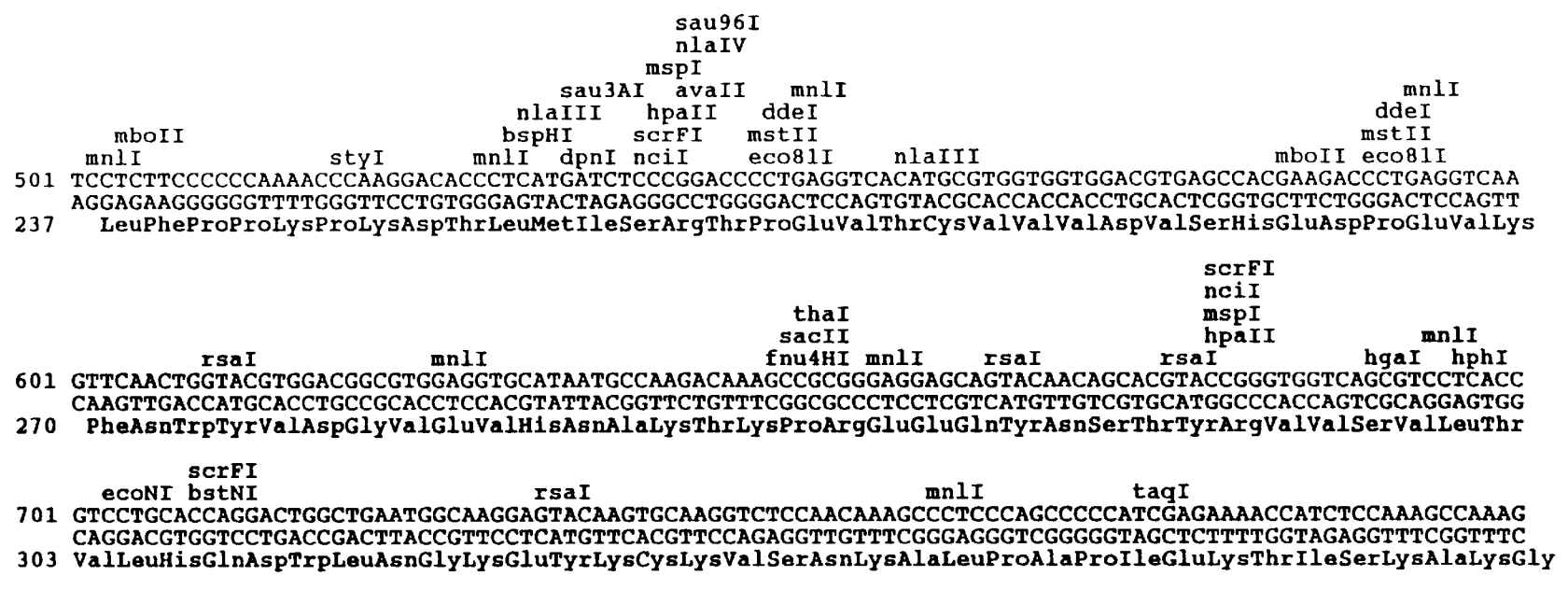
Figure 4B-2:
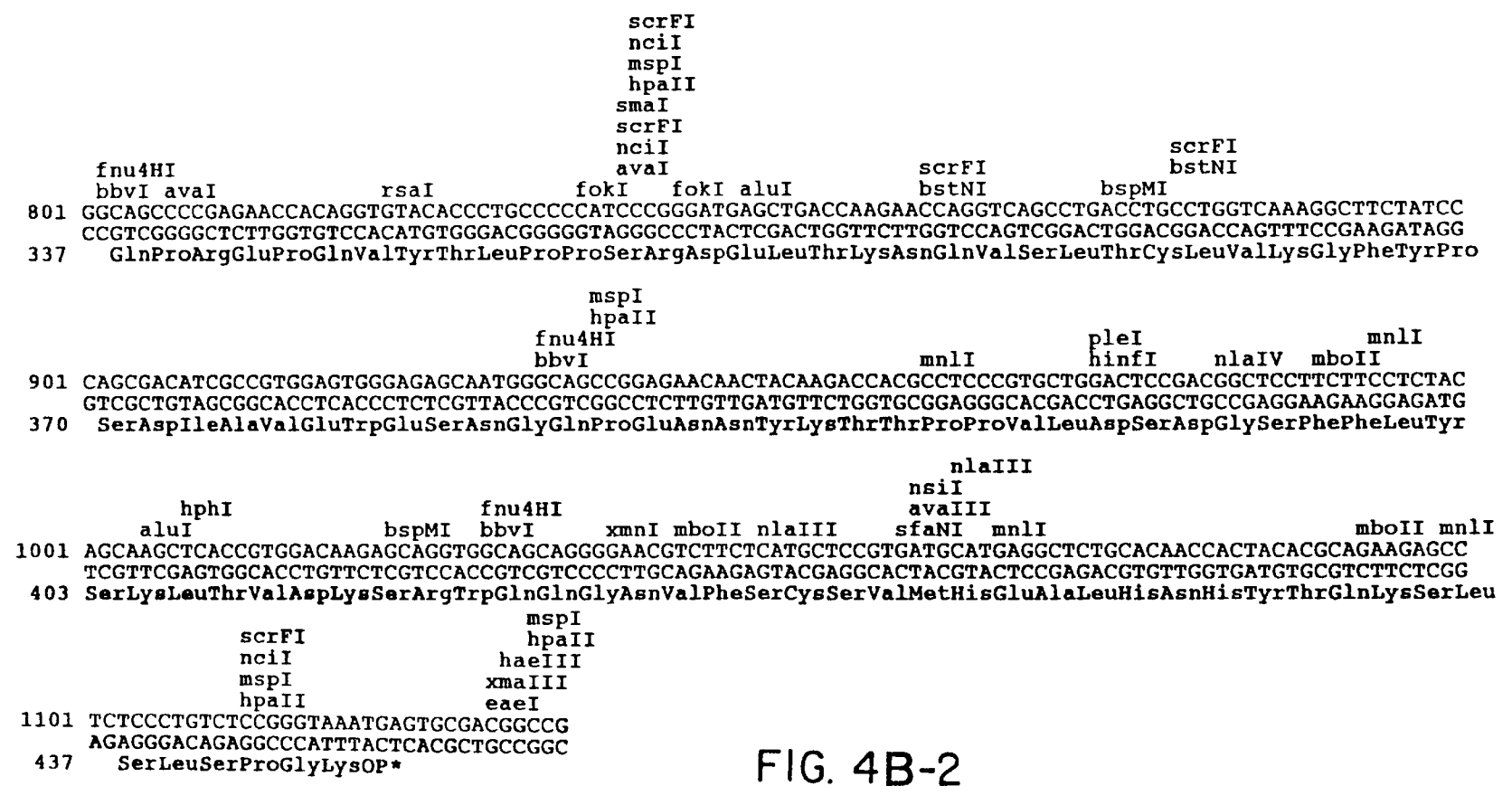

FIGS. 4A, 4B-1, and 4B-2 are a map of the linkered human IgG$_1$ ($\gamma_1$) chain fragment employed in the preparation of CD4 fusions (SEQ ID NOS:7–9 for amino acid and nucleotide sequences, respectively). Insert sites are designated γ1 and Fc.

Figure 5:
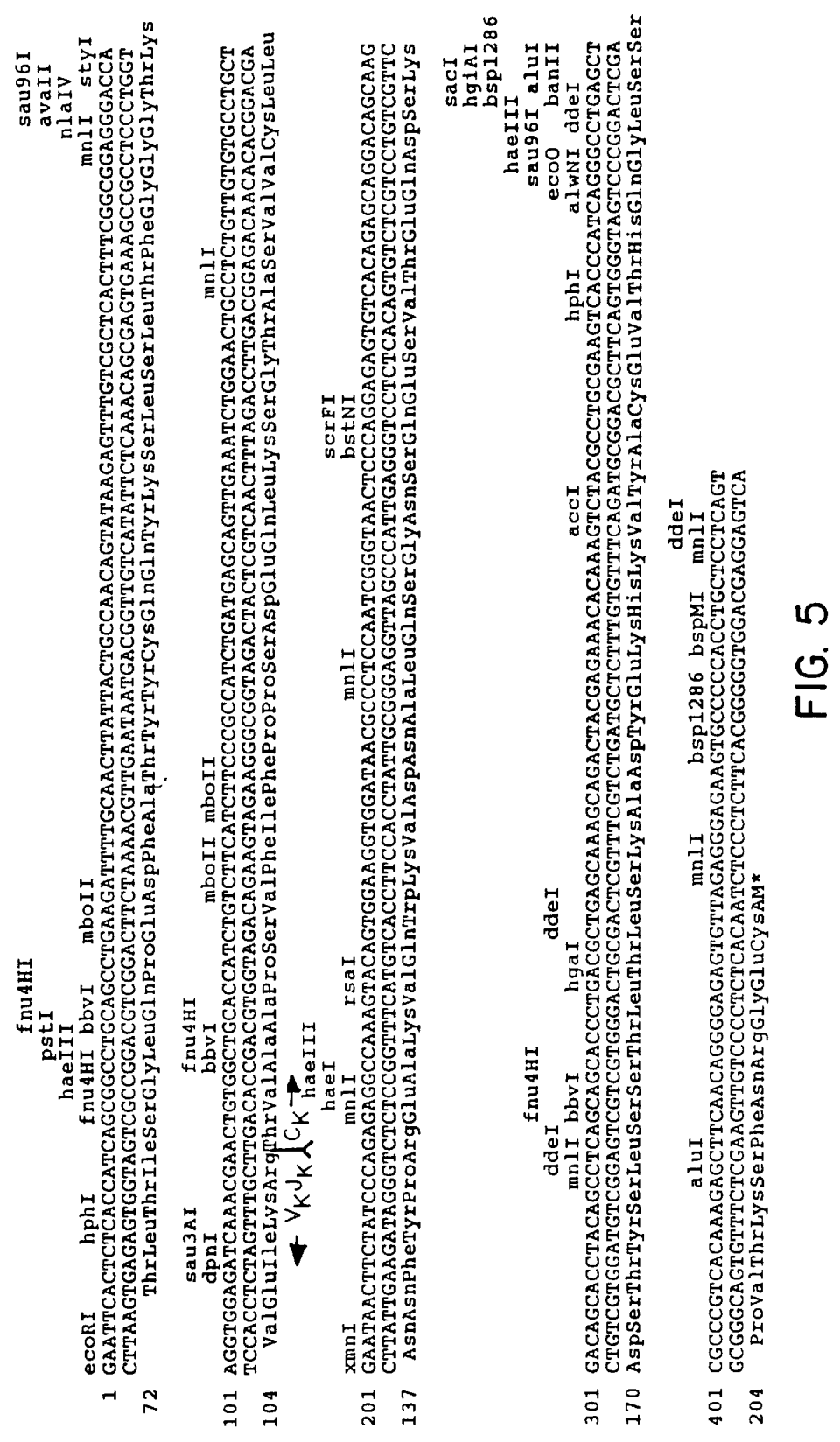

FIG. 5 is a map of the human κ light chain fragment useful for CD4 fusions at the arrow flanked by VκJκ (light variable and joining) and Cκ (light constant) (SEQ ID NOS:10–12 for amino acid and nucleotide sequences, respectively).

DETAILED DESCRIPTION

Figure 3:
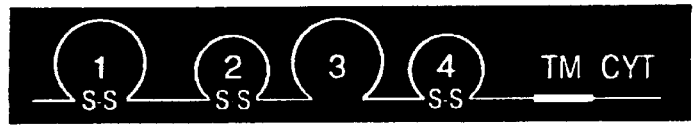
FIG. 3 depicts the structural elements of the native and soluble CD4 adheson, the native human IgG$_1$ ($\gamma_1$) heavy chain and two exemplary heavy chain-CD4 chimeras.
Figure 3:
Figure 3:
Figure 3:
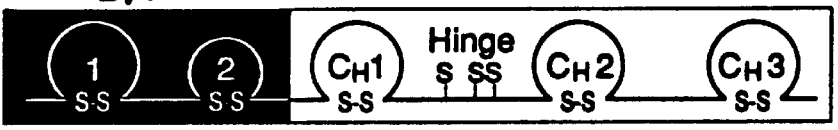
Figure 3:

Adhesons are cell surface polypeptides having an extracellular domain which is homologous to a member of the immunoglobulin gene superfamily, excluding, however, highly polymorphic members of this superfamily selected from the group of class I and class II major histocompatibility antigens, immunoglobulins and T-cell receptor α, β, γ and δ chains. Examples of adhesons include CD1, CD2, CD4, CD8, CD28, the γ, δ and ε chains of CD3, OX-2, Thy-1, the intercellular or neural cell adhesion molecules (I-CAM or N-CAM), lymphocyte function associated antigen-3 (LFA-3), neurocytoplasmic protein (NCP-3), poly-Ig receptor, myelin-associated glycoprotein (MAG), high affinity IgE receptor, the major glycoprotein of peripheral myelin (Po), platelet derived growth factor receptor, colony stimulating factor-1 receptor, macrophage Fc receptor, Fc gamma receptors and carcinoembryonic antigen. Homologous as defined herein means having the sequence of a member of the immunoglobulin gene superfamily or having a sequence therewithin which has substantially the same as (or a greater degree of) amino acid sequence homology to a known member of the superfamily as the specific examples given above have to the sequence of an immunoglobulin variable or constant domain. Preferred adhesons are CD4, CD8 and high affinity IgE Fc receptor.

This invention is particularly concerned with amino acid sequence variants of adhesons. Amino acid sequence variants of adhesons are prepared with various objectives in mind, including increasing the affinity of the adheson for its binding partner, facilitating the stability, purification and preparation of the adheson, increasing its plasma half life, improving therapeutic efficacy as described above in the background, and introducing additional functionalities and lessening the severity or occurrence of side effects during therapeutic use of the adheson. Amino acid sequence variants of adhesons fall into one or a combination of the following classes: insertional, substitutional or deletional variants.

Insertional amino acid sequence variants are those in which one or more amino acid residues extraneous to the adheson are introduced into a predetermined site in the adheson including the C- or N-termini. Such variants are referred to as fusions of the adheson and a different polypeptide. Such other polypeptides contain sequences other than those which are normally found in the adheson at the inserted position. Several groups of fusions are contemplated herein. Immunologically active adheson fusions comprise an adheson and a polypeptide containing a non-adheson epitope. The non-adheson pitope is any immunologically competent polypeptide, i.e., any polypeptide which is capable of eliciting an immune response in the animal to which the fusion is to be administered or which is capable of being bound by an antibody raised against the non-adheson polypeptide. Typical non-adheson epitopes will be those which are borne by allergens, autoimmune epitopes, or other potent immunogens or antigens recognized by pre-existing antibodies in the fusion recipient, including bacterial polypeptides such as trpLE, beta-galactosidase, viral polypeptides such as herpes gD protein, and the like. Immunogenic fusions are produced by cross-linking in vitro or by recombinant cell culture transformed with DNA encoding an immunogenic polypeptide. It is preferable that the immunogenic fusion be one in which the immunogenic sequence is joined to or inserted into the adheson antigen or fragment thereof by a peptide bond(s). These products therefore consist of a linear polypeptide chain containing adheson epitopes and at least one epitope foreign to the adheson. It will be understood that it is within the scope of this invention to introduce the epitopes anywhere within the adheson molecule or fragment thereof. Such fusions are conveniently made in recombinant host cells or by the use of bifunctional cross-linking agents. The use of a cross-linking agent to fuse the adheson to the immunogenic polypeptide is not as desirable as a linear fusion because the cross-linked products are not as easily synthesized in structurally homogeneous form.

These immunogenic insertions are particularly useful when formulated into a pharmacologically acceptable carrier and administered to a subject in order to raise antibodies against the adheson, which antibodies in turn are useful in diagnostics or in purification of adheson by immunoaffinity techniques known per se. Alternatively, in the purification of adhesons, binding partners for the fused non-adheson polypeptide, e.g. antibodies, receptors or ligands, are used to adsorb the fusion from impure admixtures, after which the fusion is eluted and, if desired, the adheson is recovered from the fusion, e.g. by enzymatic cleavage.

Other fusions, which may or may not also be immunologically active, include fusions of the adheson sequence with a signal sequence heterologous to the adheson, fusions of transmembrane-modified CD4 adhesons, for example, to polypeptides having enhanced plasma half life (ordinarily >about 20 hours) such as immunoglobulin chains or fragments thereof, and fusions with cytotoxic functionalities. Signal sequence fusions are employed in order to more expeditiously direct the secretion of the adheson. The heterologous signal replaces the native adheson signal, and when the resulting fusion is recognized, i.e. processed and cleaved by the host cell, the adheson is secreted. Signals are selected based on the intended host cell, and may include bacterial yeast, mammalian and viral sequences. The herpes gD glycoprotein signal is suitable for use in mammalian expression systems.

Plasma proteins which have enhanced plasma half-life longer than that of transmembrane modified CD4 include serum albumin, immunoglobulins, apolipoproteins, and transferrin. Preferably, the adheson-plasma protein fusion is not significantly immunogenic in the animal in which it is used and the plasma protein does not cause undesirable side effects in patients by virtue of its normal biological activity.

In a specific embodiment the adheson immunoglobulin-like domain which may be homologous either to the constant or to the variable region domains is conjugated with an immunoglobulin constant region sequence. The resulting products are referred to herein as immunoadhesons. Immunoglobulins and certain variants thereof are known and many have been prepared in recombinant cell culture. For example, see U.S. Pat. No. 4,745,055; EP 256,654; Faulkner et al., Nature 298:286 (1982); EP 120,694; EP 125,023; Morrison, J. Immun. 123:793 (1979); Kohler et al., P.N.A.S. USA 77:2197 (1980); Raso et al., Cancer Res. 41:2073 (1981); Morrison et al., Ann. Rev. Immunol. 2:239 (1984); Morrison, Science 229:1202 (1985); Morrison et al., P.N.A.S. USA 81:6851 (1984); EP 255,694; EP 266,663; and WO 88/03559. Reassorted immunoglobulin chains also are known. See for example U.S. Pat. No. 4,444,878; WO 88/03565; and EP 68,763 and references cited therein.

Ordinarily, the domains of adhesons that are homologous to immunoglobulins and extracellular in their native environment are fused C-terminally to the N-terminus of the constant region of immunoglobulins in place of the variable region(s) thereof, retaining at least functionally active hinge, CH2 and CH3 domains of the constant region of an immunoglobulin heavy chain. This ordinarily is accomplished by constructing the appropriate DNA sequence and expressing it in recombinant cell culture. Immunoglobulins and other polypeptides having enhanced plasma half life are fused to the extracellular or ligand binding domains of other adhesons in the same fashion.

The boundary domains for the CD4 V-like regions (V1–V4) are, respectively, about 100–109, about 175–184, about 289–298, and about 360–369 (based on the precursor CD4 amino acid sequence in which the initiating met is –25; FIG. 1A). CD4 sequences containing any of the CD4 V domains are fused to the immunoglobulin sequence. It is preferable that the V1V2 or V1V2V3V4 be fused at their C-termini to the immunoglobulin constant region. The precise site at which the fusion is made is not critical; the boundary domains noted herein are for guidance only and other sites neighboring or within the V regions may be selected in order to optimize the secretion or binding characteristics of the CD4. The optimal site will be determined by routine experimentation. In general, it has been found that the fusions are expressed intracellularly, but a great deal of variation is encountered in the degree of secretion of the fusions from recombinant hosts. For instance, the following table demonstrates the various immunoglobulin fusions that have been obtained by the method of this invention. In all examples of CD4 immunoadhesons, the CD4 signal was used to direct secretion from 293 cells. Lower case m represents murine origin, while the lower case h designates human origin. V and C are abbreviations for immunoglobulin variable and constant domains, respectively. The numerical subscripts indicate the number of parenthetical units found in the designated multimer. It will be understood that the chains of the multimers are believed to be disulfide bonded in the same fashion as native immunoglobulins. The CD4 immunoadhesons typically contained either the first N-terminal 366 residues of CD4 ($CD4_4$) or the first 180 N-terminal residues of CD4 ($CD4_2$) linked at their C-terminus to the κ (light) chain or IgG1 heavy chain constant region ($\gamma 1$).

TABLE I

| Transfected Gene | Secreted Product |
| --- | --- |
| $mV_K C_K$ | $mV_K C_K$ and/or $(mV_K C_K)_2$ |
| $mV_{\gamma 1} C_{\gamma 1}$ | ND |
| $mV_K C_K + mV_{\gamma 1} C_{\gamma 1}$ | $(mV_K C_K)_2 (mV_{\gamma 1} C_{\gamma 1})_2$ + $mV_K C_K$ and/or $(mV_K C_K)_2$ |
| hCD4-$mC_K$ | hCD4-$mC_K$ and/or (hCD4-$mC_K$)$_2$ |
| hCD4-$mC_{\gamma 1}$ | ND |
| hCD4-$mC_K$ + hCD4-$mC_{\gamma 1}$ | (hCD4-$mC_K$)$_2$(hCD4-$mC_{\gamma 1}$)$_2$ + hCD4-$mC_K$ and/or (hCD4-$mC_K$)$_2$ |
| hCD4-$hC_K$ | hCD4-$hC_K$ and/or (hCD4-$hC_K$)$_2$ |
| hCD4-$hC_{\gamma 1}$ | (hCD4-$hC_{\gamma 1}$)$_2$ |
| hCD4-$hC_K$ + hCD4-$hC_{\gamma 1}$ | (hCD4-$hC_K$)$_2$(hCD4-$hC_{\gamma 1}$)$_2$ + hCD4-$hC_K$ and/or (hCD4-$hC_K$)$_2$ |
| $mV_K C_K$ + hCD4-$hC_{\gamma 1}$ | $(mV_K C_K)_2$(hCD4-$hC_{\gamma 1}$)$_2$ + $mV_K C_K$ and/or $(mV_K C_K)_2$ |

*ND = Not detected

It is interesting to observe from this table that the CD4-human heavy chain immunoadheson was secreted as a dimer whereas the analogous murine construction was not detected (this not excluding the intracellular accumulation of the protein, however). The ability of the hCD4-$hC_\gamma 1$ transformants to produce heavy chain dimer was unexpected since previous work had suggested that immunoglobulin heavy chains are not secreted unless the hosts are cotransformed with nucleic acid encoding both heavy and light chain (Valle et al., Nature 241:338 [1981]). According to this invention, CD4-IgG immunoadheson chimeras are readily secreted wherein the CD4 epitope is present in heavy chain dimers, light chain monomers or dimers, and heavy and light chain heterotetramers wherein the CD4 epitope is present fused to one or more light or heavy chains, including heterotetramers wherein up to and including all four variable region analogues are derived from CD4. Where light-heavy chain non-CD4 variable domain is present, a heterofunctional antibody thus is provided.

Various exemplary hetero-and chimeric immunoadheson antibodies produced in accordance with this invention are schematically diagrammed below. "A" means at least a portion of the extracellular domain of an adheson containing its ligand binding site; $V_L$, $V_H$, $C_L$ and $C_H$ represent light or heavy chain variable or constant domains of an immunoglobulin; n is an integer; and Y designates a covalent cross-linking moiety.

(a) $AC_L$;
(b) $AC_L$-$AC_L$;
(c) $AC_H$-[$AC_H$, $AC_L$-$AC_H$, $AC_L$-$V_H C_H$, $V_L C_L$-$AC_H$, or $V_L C_L$-$V_H C_H$];
(d) $AC_L$-$AC_H$-[$AC_H$, $AC_L$-$AC_H$, $AC_L$-$V_H C_H$, $V_L C_L$-$AC_H$, or $V_L C_L$-$V_H C_H$];
(e) $AC_L$-$V_H C_H$-[$AC_H$, $AC_L$-$AC_H$, $AC_L$-$V_H C_H$, $V_L C_L$-$AC_H$, or $V_L C_L$-$V_H C_H$];
(f) $V_L C_L$-$AC_H$-[$AC_H$, $AC_L$-$AC_H$, $AC_L$-$V_H C_H$, $V_L C_L$-$AC_H$, or $V_L C_L$-$V_H C_H$]; or
(g) $[A-Y]_n$-$[V_L C_L$-$V_H C_H]_2$.

The structures shown in this table show only key features, e.g. they do not show joining (J) or other domains of the immunoglobulins, nor are disulfide bonds shown. These are omitted in the interests of brevity. However, where such domains are required for binding activity they shall be construed as being present in the ordinary locations which they occupy in the adheson, immunoadheson or immunoglobulin molecules as the case may be. These examples are representative of divalent antibodies; more complex structures would result by employing immunoglobulin heavy chain sequences from other classes, e.g. IgM. The immunoglobulin $V_L V_H$ antibody combining site, also designated as the companion immunoglobulin, preferably is capable of binding to a predetermined antigen.

Suitable companion immunoglobulin combining sites and fusion partners are obtained from IgG-1, -2, -3, or -4 subtypes, IgA, IgE, IgD or IgM, but preferably IgG-1.

A preferred embodiment is a fusion of an N-terminal portion of CD4, which contains the binding site for the gp120 envelope protein of HIV, to the C-terminal $F_c$ portion of an antibody, containing the effector functions of immunoglobulin $G_1$. There are two preferred embodiments of this sort; in one, the entire heavy chain constant region is fused to a portion of CD4; in another, a sequence beginning in the hinge region just upstream of the papain cleavage site which defines IgG F, chemically (residue 216, taking the first residue of heavy chain constant region to be 114 [Kobat et al., "Sequences of Proteins of Immunological Interest" 4th Ed., 1987], or analogous sites of other immunoglobulins) is fused to a portion of CD4. These embodiments are described in the examples.

More particularly, those variants in which one or more immunoglobulin-like domains of an adheson are substituted for the variable region of an immunoglobulin chain are believed to exhibit improved in vivo plasma half life. These chimeras are constructed in a fashion similar to chimeric antibodies in which a variable domain from an antibody of one species is substituted for the variable domain of another species. See, for example, EP 0 125 023; Munro, Nature 312: (Dec. 13, 1984); Neuberger et al., Nature 312: (Dec. 13, 1984); Sharon et al., Nature 309: (May 24, 1984); Morrison et al., Proc. Natl. Acad. Sci. USA 81:6851–6855 (1984); Morrison et al. Science 229:1202–1207 (1985); and Boulianne et al., Nature 312:643–646 (Dec. 13, 1984). The DNA encoding the adheson immunoglobulin-like domain(s) is cleaved by a restriction enzyme at or proximal to the 3' end of the DNA encoding the immunoglobulin-like domain(s) and at a point at or near the DNA encoding the N-terminal end of the mature adheson polypeptide (where use of a different leader is contemplated) or at or proximal to the N-terminal coding region for the adheson (where the native adheson signal is employed). This DNA fragment then is readily inserted into DNA encoding an immunoglobulin light or heavy chain constant region and, if necessary, tailored by deletional mutagenesis. Preferably, this is a human immunoglobulin when the variant is intended for in vivo therapy for humans. DNA encoding immunoglobulin light or heavy chain constant regions is known or readily available from cDNA libraries or is synthesized. See, for example, Adams et al., Biochemistry 19:2711–2719 (1980); Gough et al., Biochemistry 19:2702–2710 (1980); Dolby et al., P.N.A.S. USA, 77:6027–6031 (1980); Rice et al., P.N.A.S. USA 79:7862–7865 (1982); Falkner et al., Nature 298:286–288 (1982); and Morrison et al., Ann. Rev. Immunol. 2:239–256 (1984).

DNA encoding the immunoglobulin or immunoadheson chimeric chain(s) is transfected into a host cell for expression. If the host cell is producing an immunoglobulin prior to transfection then one need only transfect with the adheson fused to light or to heavy chain to produce a heteroantibody. The aforementioned immunoglobulins having one or more arms bearing the adheson domain and one or more arms bearing companion variable regions result in dual specificity for adheson ligand and for an antigen. These are produced by the above-described recombinant methods or by in vitro procedures. In the latter case, for example, F(ab')$_2$ fragments of the adheson fusion and an immunoglobulin are prepared, the F(ab')2 fragments converted to Fab' fragments by reduction under mild reducing conditions, and then reoxidized in each other's presence under acidic conditions in accord with methods known per se. See also U.S. Pat. No. 4,444,878.

Additionally, procedures are known for producing intact heteroantibodies from immunoglobulins having different specificities. These procedures are adopted for the in vitro production of heterochimeric antibodies by simply substituting the immunoadheson chains for one of the previously employed immunoglobulins.

In an alternative method for producing a heterofunctional antibody, host cells producing an adheson-immunoglobulin fusion, e.g. transfected myelomas, also are fused with B cells or hybridomas which secrete antibody having the desired companion specificity for an antigen. Heterobifunctional antibody is recovered from the culture medium of such hybridomas, and thus may be produced somewhat more conveniently than by conventional in vitro resorting methods (EP 68,763).

Another group of fusions are those in which an adheson is conjugated with a toxic substance, e.g. a polypeptide such as ricin (including deglycosylated ricin A chain), diptheria toxin A, or a non-peptidyl cytotoxin. Where the toxin is a polypeptide it is convenient to cross-link the polypeptide to the adheson or its transmembrane-deleted variant by conventional in vitro protein cross-linking agents (for suitable methods for linking ricin A chain or deglycosylated A chain to CD4 see, for example, Duncan et al., "Analy. Biochem." 132:68–73 [1983]; Thorpe et al., "Cancer Res." 47:5924 [1987]; and Ghotie et al., "Cancer Res." 48:2610 [1988]) or by recombinant synthesis as a fusion (see for example, U.S. Pat. No. 4,765,382). Alternatively, where companion antibodies are anti-ricin antibody immunoglobulin variable domains, such immunoglobulin heteroantibodies are employed to deliver ricin to HIV infected cells following the general procedure of Raso et al., Cancer Research, 41:2073 (1981).

Another class of adheson variants are deletional variants. Deletions are characterized by the removal of one or more amino acid residues from an adheson sequence. Typically, the transmembrane and cytoplasmic domains of adhesons are deleted. In the case of CD4, at least residues 368 to 395 (the transmembrane region), and ordinarily 396–433 as well (the cytoplasmic domain), will be deleted to obtain secreted forms of this adheson. Parenthetically, the amino acid residues follow the numbers given for mature CD4 as noted, for example, in FIGS. 1A–1C. Thus, CD4T molecules generally will terminate in the vicinity of about residues 366–368, or at any other suitable site N-terminal thereto which preserves the gp120-binding capability of the CD4 variant.

Substitutional variants are those in which at least one residue in the adheson sequence has been removed and a different residue inserted in its place. The native N-terminal residue for mature CD4 is now known to be lysine. Thus, the sequence shown in FIG. 1, with an N-terminal asparagine, is an amino acid sequence variant of native mature CD4. Table II below describes substitutions which in general will result in fine modulation of the characteristics of the CD antigen.

TABLE II

| Original Residue | Exemplary Substitutions |
| --- | --- |
| Ala | ser |
| Arg | lys |
| Asn | gln; his |
| Asp | glu |
| Cys | ser; ala |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table II, i.e., selecting residues that differ more significantly in their effect on maintaining (a) the structure of the polypeptide backbone in the area of the substitution, for example, as a sheet or helical conformation, (b) the charge or hydrophobicity of the molecule at the target site or (c) the bulk of the side chain. The substitutions which in general are expected to produce the greatest changes in adheson properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteinyl or prolyl is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanyl, is substituted for (or by) one not having a side chain, e.g., glycyl.

A preferred class of substitutional or deletional variants are those involving the transmembrane region of the adheson. The transmembrane region of the adheson is a highly hydrophobic or lipophilic domain that is the proper size to span the lipid bilayer of the cellular membrane. It is believed to anchor the adheson in the cell membrane.

Deletion or substitution of the transmembrane domain will facilitate recovery and provide a soluble form of the adheson by reducing its cellular or membrane lipid affinity and improving its water solubility. If the transmembrane and cytoplasmic domains are deleted one avoids the introduction of potentially immunogenic epitopes, either by exposure of otherwise intracellular polypeptides that might be recognized by the body as foreign or by insertion of heterologous polypeptides that are potentially immunogenic. A principal advantage of the transmembrane deleted adheson is that it is secreted into the culture medium of recombinant hosts. This variant is water soluble and does not have an appreciable affinity for cell membrane lipids, thus considerably simplifying its recovery from recombinant cell culture.

It will be amply apparent from the foregoing discussion that substitutions, deletions, insertions or any combination thereof are introduced to arrive at a final construct. As a general proposition, all variants will not have a functional transmembrane domain and preferably will not have a functional cytoplasmic sequence. This is generally accomplished by deletion of the relevant domain, although adequate insertional or substitutional mutagens also can be effective for this purpose. For example, the transmembrane domain is substituted by any amino acid sequence, e.g. a random or homopolynucleic sequence of about 5 to 50 serine, threonine, lysine, arginine, glutamine, aspartic acid and like hydrophilic residues, which altogether exhibit a hydrophilic hydropathy profile, so that it is secreted into the culture medium of recombinant hosts. This variant should also be considered to be an adheson variant.

These variants ordinarily are prepared by site specific mutagenesis of nucleotides in the DNA encoding the adheson, thereby producing DNA encoding the variant, and thereafter expressing the DNA in recombinant cell culture. However, variant adhesons also are prepared by in vitro synthesis. Obviously, variations made in the DNA encoding the variant adhesons must not place the sequence out of reading frame and preferably will not create complementary regions that could produce secondary mRNA structure deleterious to expression (EP 75,444A). The CD4 variants typically exhibit the same gp120 binding activity as does the naturally-occurring prototype, although variants also are selected in order to modify the characteristics of the CD4 adheson as indicated above.

While the site for introducing an amino acid sequence variation is predetermined, the mutation per se need not be predetermined. For example, in order to optimize the performance of a mutation at a given site, random mutagenesis may be conducted at the target codon or region and the expressed adheson variants screened for the optimal combination of desired activities. Techniques for making substitution mutations at predetermined sites in DNA having a known sequence are well known, for example, M13 primer mutagenesis.

Adheson variants that are not capable of binding HIV gp120 are useful nonetheless as immunogens for raising antibodies to the adheson or as immunoassay kit components (labelled, as a competitive reagent for gp120 assay, or unlabelled as a standard for an adheson assay) so long as at least one adheson epitope remains active.

The DNA encoding adhesons is obtained by known procedures. See Williams, Immunol. Today 8:298–303 (1987) and citations therein. In general, prokaryotes are used for cloning of CD4 variant DNA sequences. For example, *E. coli* strain SR101 (for propagating M13 phage, a λ-resistant strain of JM 101; Messing et al., Nucl. Acids. Res. 9(2):309–321 [1981]); and *E. coli* K12 strain 294 (ATCC No. 31446) are particularly useful. Other microbial strains which may be used include *E. coli* B, UM101 and *E. coli* x1776 (ATCC No. 31537). These examples are illustrative rather than limiting.

DNA encoding the variant adhesons is inserted for expression into vectors containing promoters and control sequences which are derived from species compatible with the intended host cell. The vector ordinarily, but need not, carry a replication site as well as one or more marker sequences which are capable of providing phenotypic selection in transformed cells. For example, *E. coli* is typically transformed using a derivative of pBR322 which is a plasmid derived from an *E. coli* species (Bolivar, et al., Gene 2: 95 [1977]). pBR322 contains genes for ampicillin and tetracycline resistance and thus provides easy means for identifying transformed cells. The pBR322 plasmid, or other microbial plasmid, must also contain or be modified to contain promoters and other control elements commonly used in recombinant DNA constructions.

Promoters suitable for use with prokaryotic hosts illustratively include the β-lactamase and lactose promoter systems (Chang et al., Nature, 275: 615 [1978]; and Goeddel et al., Nature 281: 544 [1979]), alkaline phosphatase, the tryptophan (trp) promoter system (Goeddel, Nucleic Acids Res. 8: 4057 [1980] and EPO Appln. Publ. No. 36,776) and hybrid promoters such as the tac promoter (H. de Boer et al., Proc. Natl. Acad. Sci. USA 80: 21–25 [1983]). However, other functional bacterial promoters are suitable. Their nucleotide sequences are generally known, thereby enabling a skilled worker operably to ligate them to DNA encoding the adheson variant using linkers or adaptors to supply any required restriction sites (Siebenlist et al., Cell 20: 269 [1980]). Promoters for use in bacterial systems also will contain a Shine-Dalgarno (S.D.) sequence operably linked to the DNA encoding the antigen.

In addition to prokaryotes, eukaryotic microbes such as yeast cultures also are useful as cloning or expression hosts. *Saccharomyces cerevisiae*, or common baker's yeast, is the most commonly used eukaryotic microorganism, although a number of other strains are commonly available. For expression in Saccharomyces, the plasmid YRp7, for example, (Stinchcomb, et al., Nature 282: 39 [1979]; Kingsman et al, Gene 7: 141 [1979]; Tschemper et al., Gene 10: 157 [1980]) is commonly used. This plasmid already contains the trp1 gene which provides a selection marker for a mutant strain of yeast lacking the ability to grow in tryptophan, for example ATCC no. 44076 or PEP4-1 (Jones, Genetics 85: 12 [1977]). The presence of the trp1 lesion as a characteristic of the yeast host cell genome then provides an effective means of selection by growth in the absence of tryptophan.

Suitable promoting sequences for use with yeast hosts include the promoters for 3-phosphoglycerate kinase (Hitzeman et al., J. Biol. Chem. 255: 2073 [1980]) or other glycolytic enzymes (Hess et al., J. Adv. Enzyme Reg. 7: 149 [1968]; and Holland, Biochemistry 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., European Patent Publication No. 73,657A. Yeast enhancers also are advantageously used with yeast promoters.

Promoters for controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. the beta actin promoter. The early and late promoters of the SV40 virus are conveniently obtained as an SV40 restriction fragment which also contains the SV40 viral origin of replication. Fiers et al., Nature, 273: 113 (1978). The immediate early promoter of the human cytomegalovirus is conveniently obtained as a HindIII E restriction fragment. Greenaway, P. J. et al., Gene 18: 355–360 (1982). Of course, promoters from the host cell or related species also are useful herein.

DNA transcription in higher eukaryotes is increased by inserting an enhancer sequence into the vector. Enhancers are cis-acting elements of DNA, usually from about 10 to 300 bp, that act to increase the transcription initiation capability of a promoter. Enhancers are relatively orientation and position independent having been found 5' (Laimins, L. et al., Proc. Natl. Acad. Sci. 78: 993 [1981]) and 3' (Lusky, M. L., et al., Mol. Cell Bio. 3: 1108 [1983]) to the transcription unit, within an intron (Banerji, J. L. et al., Cell 33: 729 [1983]) as well as within the coding sequence itself (Osborne, T. F., et al., Mol. Cell Bio. 4: 1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding the adheson.

Expression vector systems generally will contain a selection gene, also termed a selectable marker. Examples of suitable selectable markers for mammalian cells are dihydrofolate reductase (DHFR), thymidine kinase or neomycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented medium. Two examples are: CHO DHFR-cells and mouse LTK-cells.

These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented medium. An alternative to supplementing the medium is to introduce an intact DHFR or TK gene into cells lacking the respective genes, thus altering their growth requirements. Individual cells which were not transformed with the DHFR or TK gene will not be capable of survival in non-supplemented media.

The second category is dominant selection, which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern P. and Berg, P., J. Molec. Appl. Genet. 1: 327 [1982]), mycophenolic acid (Mulligan, R. C. and Berg, P. Science 209: 1422 [1980]) or hygromycin (Sugden, B. et al., Mol. Cell. Biol. 5: 410–413 [1985]). The three examples given above employ bacterial genes under eukaryotic control to convey resistance to the appropriate drug G418 or neomycin (geneticin), xgpt (mycophenolic acid) or hygromycin, respectively.

"Amplification" refers to the increase or replication of an isolated region within a cell's chromosomal DNA. Amplification is achieved using a selection agent e.g. methotrexate (MTX) which inactivates DHFR. Amplification or the making of successive copies of the DHFR gene results in greater amounts of DHFR being produced in the face of greater amounts of MTX. Amplification pressure is applied notwithstanding the presence of endogenous DHFR, by adding ever greater amounts of MTX to the media. Amplification of a desired gene can be achieved by cotransfecting a mammalian host cell with a plasmid having a DNA encoding a desired protein and the DHFR or amplification gene permitting cointegration. One ensures that the cell requires more DHFR, which requirement is met by replication of the selection gene, by selecting only for cells that can grow in the presence of ever-greater MTX concentration. So long as the gene encoding a desired heterologous protein has cointegrated with the selection gene, replication of this gene gives rise to replication of the gene encoding the desired protein. The result is that increased copies of the gene, i.e. an amplified gene, encoding the desired heterologous protein express more of the desired heterologous protein. Preferred host cells for expressing the CD antigen variants of this invention are mammalian cell lines, examples including: monkey kidney CV1 line transformed by SV40 (COS-7, ATCC CRL 1651); human embryonic kidney line (293, Graham, F. L. et al., J. Gen Virol. 36: 59 [1977] and 293S cells [293 subclones selected for better suspension growth]); baby hamster kidney cells (BHK, ATCC CCL 10); chinese hamster ovary-cells-DHFR (CHO, Urlaub and Chasin, Proc. Natl. Acad. Sci. (USA) 77: 4216, [1980]); mouse sertoli cells (TM4, Mather, J. P., Biol. Reprod. 23: 243–251 [1980]); monkey kidney cells (CV1 ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL51); and TRI cells (Mather, J.P. et al., Annals N.Y. Acad. Sci. 383: 44–68 [1982]).

"Transformation" means introducing DNA into an organism so that the DNA is replicable, either as an extrachromosomal element or by chromosomal integration. One suitable transformation of the host cells is the method of Graham, F. and van der Eb, A., Virology 52: 456–457 (1973). However, other methods for introducing DNA into cells such as by nuclear injection or by protoplast fusion may also be used. If prokaryotic cells or cells which contain substantial cell walls are used as hosts, the preferred method of transfection is calcium treatment using calcium chloride as described by Cohen, F. N. et al., Proc. Natl. Acad. Sci. (USA), 69: 2110 (1972).

Construction of suitable vectors containing the desired coding and control sequences employs standard and manipulative ligation techniques. Isolated plasmids or DNA fragments are cleaved, tailored, and religated in the form desired to form the plasmids required. Suitable procedures are well known for the construction described herein. See, for example, Maniatis, T. et al., *Molecular Cloning*, 133–134 Cold Spring Harbor, (1982); "Current Protocols in Molecular Biology", edited by Ausubel et al., (1987), pub. by Greene Publishing Associates & Wiley-Interscience.

Correct plasmid sequences are confirmed by transforming *E. coli* K12 strain 294 (ATCC 31446) with ligation mixtures, successful transformants are selected by ampicillin or tetracycline resistance where appropriate, and plasmids from the transformants are prepared, and then analyzed by restriction enzyme digestion and/or sequenced by the method of Messing et al., Nucleic Acids Res. 9: 309 (1981) or by the method of Maxam et al., Methods in Enzymology 65: 499 (1980).

Host cells are transformed with the expression vectors of this invention. Thereafter they are cultured in appropriate culture media, e.g. containing substances for inducing promoters, selecting transformants or amplifying genes. The culture conditions, such as temperature, pH and the like, are those previously used with the host cell selected for expression, and will be apparent to the ordinarily skilled artisan.

The secreted adheson variants are recovered and purified from the culture supernatants or lysates of recombinant hosts.

Typically, the supernatants are concentrated by ultrafiltration, contacted with a ligand affinity or immunoaffinity matrix so as to adsorb the adheson variant, and eluted from the matrix. Optionally, the adheson is purified by ion exchange chromatography.

Surprisingly, purification of soluble CD4 adheson from culture medium was unexpectedly difficult. Notwithstanding that the hydrophobic transmembrane region of the antigen had been deleted, the antigen exhibited a strong tendency to form aggregates that could be readily removed from suspension by centrifugation at 1000 × g, and which avidly coat surfaces such as ultrafiltration membranes. This appears to result from the reduction in concentration of albumin or other serum protein (ordinarily present in the crude preparation) to a particular level, below which the truncated antigen no longer remains soluble. This phenomenon appears to be aggravated by exposure of the CD4 adheson to low pH (<about pH 4). As a result, separation procedures (particularly those that employ acid elution, such as immunoaffinity) should be modified so that the eluate is maintained at, or immediately returned to, about neutrality. Further, a surfactant, e.g. a detergent such as Tween 80, should be included with the antigen during the separation procedure. The final purified product will be stabilized with a predetermined protein such as albumin, and/or a detergent.

The purified adheson is formulated into conventional pharmacologically acceptable excipients.

It is administered to patients having HIV infection at a dosage capable of maintaining a concentration of greater than about 100 ng of soluble CD4 adheson/ml plasma. For CD4 adheson variants having different molecular weights, about 2 picomoles of soluble receptor per ml of plasma will be initially evaluated clinically in order to establish a stoichiometric equivalence with native (membrane bound) and soluble receptor. The ordinary dosage of soluble CD4 is 100 μg/kg of patient weight/day.

The therapeutic CD4 variants are employed with other therapies and agents for the treatment of AIDS, including AZT, neutralizing antibodies and immunocytotoxins, gp120 fragments and vaccines.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements are used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally (Lawn, R. et al., Nucleic Acids Res. 9: 6103–6114 [1981], and Goeddel, D. et al., Nucleic Acids Res. 8: 4057 [1980]).

"Dephosphorylation" refers to the removal of the terminal 5' phosphates by treatment with bacterial alkaline phosphatase (BAP). This procedure prevents the two restriction cleaved ends of a DNA fragment from "circularizing" or forming a closed loop that would impede insertion of another DNA fragment at the restriction site. Procedures and reagents for dephosphorylation and other recombinant manipulations are conventional. Reactions using BAP are carried out in 50 mM Tris at 68° C. to suppress the activity of any exonucleases which may be present in the enzyme preparations. Reactions are run for 1 hour. Following the reaction the DNA fragment is gel purified.

"Ligation" refers to the process of forming phosphodiester bonds between two double stranded nucleic acid fragments (Maniatis, T. et al., Id. at 146). Unless otherwise provided, ligation may be accomplished using known buffers and conditions with 10 units of T4 DNA ligase ("ligase") per 0.5 μg of approximately equimolar amounts of the DNA fragments to be ligated.

"Filling" or "blunting" refers to the procedures by which the single stranded end in the cohesive terminus of a restriction enzyme-cleaved nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminus. Typically, blunting is accomplished by incubating 2–15 μg of the target DNA in 10 mM $MgCl_2$, 1 mM dithiothreitol, 50 mM NaCl, 10 mM Tris (pH 7.5) buffer at about 37° C. in the presence of 8 units of the Klenow fragment of DNA polymerase I and 250 7μm of each of the four deoxynucleoside triphosphates. The incubation generally is terminated after 30 min. and the reaction mixture is subjected to phenol and chloroform extraction and ethanol precipitation.

The following examples merely illustrate the best mode now contemplated for practicing the invention, but should not be construed to limit the invention. All literature citations herein are expressly incorporated by reference.

EXAMPLE 1

Construction of Vectors for the Expression of Native CD4 and Secreted Derivatives Section 1

The plasmid used for recombinant synthesis of human CD4 was pSVeCD4DHFR. The plasmid was constructed as follows:

λCD4P1 containing most of the coding sequence of human CD4 (obtained from a human placental cDNA library using oligonucleotide probes based on the published sequence Maddon et al. (1985) was digested with EcoRI to produce the cDNA insert. This fragment was recovered by polyacrylamide gel electrophoresis (fragment 1).

pUC18 was digested with EcoRI and the single fragment recovered by polyacrylamide gel electrophoresis (fragment 2). Fragment 1 was ligated to fragment 2 and the ligation mixture transformed into E. coli strain 294. The transformed culture was plated on ampicillin media plates and resistant colonies were selected. Plasmid DNA was prepared from transformants and checked by restriction analysis for the presence of the correct DNA fragments. This plasmid is referred to as pUCCD4.

pSVeE'DHFR (Muesing et al., Cell 48:691–701 [1987]) was digested with KpnI and BamHI and blunted with E. coli DNA polymerase I (Klenow fragment) and the four dNTPs. Fragment 3 containing the pML-$Amp^r$ region, SV40 early promoter, the HIV LTR, and the mouse DHFR gene was recovered by gel electrophoresis, ligated and the ligation mixture transformed into E. coli strain 294. The transformed culture was plated on ampicillin media plates and resistant colonies selected. Plasmid DNA was prepared from transformants and checked by restriction analysis for the presence of the BamHI restriction site and the absence of the KpnI restriction site. This plasmid is referred to as pSVeΔBKDHFR and allows EcoRI-BamHI fragments to be inserted after the SV40 early promoter and transcribed under its control, following transfection into an appropriate cell line.

Synthetic oligonucleotides (adaptors 1–8, below) were made to extend from 76 bp 5' of the initiation codon of CD4 translation to the RsaI restriction site at 121 bp 3' of the initiator, with the sequence AATT at the 5' end of the sense strand to generate an end which could ligate to an EcoRI restriction fragment. These oligonucleotides were ligated and the 204 bp fragment containing the entire sequence was recovered by gel electrophoresis (fragment 4).

CD4 adaptor 1: AATTCAAGCCCAGAGCCCTGC-CATTTCTGTGGGCTCAGGTCCCT (SEQ ID NO: 13)

CD4 adaptor 2: pACTGCTCAGCCCCTTCCTCCCTCG-GCAAGGCCACAATGAACCGGGGAGTC (SEQ ID NO: 14)

CD4 adaptor 3: pCCTTTTAGGCACTTGCTTCTGGT-GCTGCAACTGGCGCTCCTCCCAGC (SEQ ID NO: 15)

CD4 adaptor 4: pAGCCACTCAGGGAAACAAAGTGGT-GCTGGGCAAAAAAGGGGATACAGTG-GAACTGACCT GT (SEQ ID NO: 16)

CD4 adaptor 5: pACAGGTCAGTTCCACTGTATC-CCCTTTTTTGCCCAGCACCACTTTGTTTCC (SEQ ID NO: 17)

CD4 adaptor 6: pCTGAGTGGCTGCTGGGAGGAGCGC-CAGTTGCAGCACCAGAAGCAAGT (SEQ ID NO: 18)

CD4 adaptor 7: pGCCTAAAAGGGACTCCCCGGTTCAT-TGTGGCCTTGCCGAGGGAGGAAGGG (SEQ ID NO: 19)

CD4 adaptor 8: GCTGAGCAGTAGGGACCTGACCCCA-CAGAAATGGCAGGGCTCTGGGCTTG (SEQ ID NO: 20)

pUCCD4 was digested with RsaI and SstI and the 401 bp fragment containing part of the CD4 coding sequence recovered by gel electrophoresis (fragment 5). pUC18 was digested with EcoRI and SstI and the fragment comprising the bulk of the plasmid recovered by gel electrophoresis (fragment 6). Fragments 4 and 5 were ligated to fragment 6 and the ligation mixture was transformed into E. coli strain 294. The transformed culture was plated on ampicillin media plates and resistant colonies were selected. Plasmid DNA was prepared from transformants and checked by restriction analysis for the presence of the correct fragment. The sequence of the inserted synthetic DNA was checked by excising the 605 bp EcoRI-SstI fragments from several transformants and ligating them to M13mp19 which had been digested with the same enzymes. After transformation into E. coli strain JM101, single-stranded DNA was prepared and sequenced. One plasmid which contained the correct sequence was selected, and is referred to as pCD4int.

pCD4int was digested with EcoRI and SstI and fragment 7 containing the 5' end of the CD4 coding region was recovered by gel electrophoresis. pUCCD4 was digested with SstI and BamHI and the 1139 bp fragment containing the remainder of the CD4 coding region (fragment 8) recovered by gel electrophoresis.

pSVeΔBKDHFR was digested with EcoRI and BamHI and fragment 9 comprising the bulk of the plasmid was isolated. Fragments 7, 8 and 9 were ligated and the ligation mixture was transformed into E. coli strain 294. The transformed culture was plated on ampicillin media plates and the resistant colonies were selected. Plasmid DNA was prepared from transformants and checked by restriction analysis for the presence of the correct fragment. This plasmid is referred to as pSVeCD4DHFR, and was used to direct synthesis of recombinant intact CD4.

Section 2

A plasmid was constructed to direct the synthesis of a CD4 derivative lacking the putative transmembrane domain and most of the putative cytoplasmic domain (Maddon et al., supra). This was done with the intention of creating a secreted form of CD4, based on the assumption that these domains anchor the CD4 glycoprotein to the cell membrane, and that their deletion would result in the secretion of the product. This plasmid is referred to as pSVeCD4ΔNlaDHFR and was constructed as follows:

pUCCD4 was digested with SstI and TaqI and the 531 bp fragment (fragment 10) recovered. pUCCD4 was digested with NlaIII and TaqI and the 112 bp fragment (fragment 11) recovered. pUCCD4 was digested with BamHI and NlaIII and the 301 bp fragment (fragment 12) recovered. pCD4int was digested with SstI and BamHI and fragment 13 comprising the bulk of the plasmid recovered. Fragments 10, 11, and 12 were ligated together with fragment 13 and the ligation mixture was transformed into E. coli strain 294. The transformed culture was plated on ampicillin media plates and resistant colonies were selected. Plasmid DNA was prepared from transformants and checked by restriction analysis for the presence of the correct fragment. Plasmid DNA from several transformants was sequenced to ensure that the 195 bp NlaIII fragment had been deleted and that the proper reading frame was restored. The resulting plasmid is referred to as pCD4ΔNla. pCD4ΔNla was digested with EcoRI and BamHI and the 1541 bp fragment containing the sequence of a CD4 derivative lacking the transmembrane and cytoplasmic domains recovered (fragment 14) and ligated to fragment 9, and the ligation mixture was transformed into E. coli strain 294. The transformed culture was plated on ampicillin media plates and resistant colonies were selected. Plasmid DNA was prepared from transformants and checked by restriction analysis for the presence of the correct fragment. This plasmid is referred to as pSVeCD4DNlaDHFR.

Both pSVeCD4DHFR and pSVeCD4ΔNlaDHFR were transfected into CHO cells by the same method used to establish cell lines stably expressing HIV-I polypeptides (Muesing, Smith and Capon, Cell 48:6910701 [1987]). These cells were assayed for production by radioimmunoprecipitation as described below. While no product was detected in initial experiments, subsequent experiments showed that the above described coding segment could indeed direct the synthesis of a soluble CD4 adheson variant both in CHO and 293 cells.

Section 3

A different expression system was initially used for the synthesis and expression of a CD4 variant lacking completely the cytoplasmic and transmembrane domains. This system uses the cytomegalovirus promoter and can be used in cultured cells of human origin. The first plasmid constructed for use in this system contained the entire coding region for CD4 and was intended to function as a control in the following studies. It is referred to as pRKCD4, and was constructed as follows:

pSVeCD4DHFR was digested with EcoRI and BamHI and fragment 15 containing the entire CD4 coding region was isolated. pRK5 (U.S. Ser. No. 97,472, filed Sep. 11, 1987, now abandoned) was digested with EcoRI and BamHI and fragment 16 comprising the bulk of the plasmid recovered by gel electrophoresis, ligated to fragment 15, and the ligation mixture transformed into E. coli strain 294. The transformed culture was plated on ampicillin media plates and resistant colonies selected. Plasmid DNA was prepared from transformants and checked by restriction analysis for the presence of the correct fragment. This plasmid is referred to as pRKCD4.

Section 4

The next plasmid constructed was designed to direct the expression of the above-mentioned (Section 3) secreted derivative of CD4. The coding region of CD4 was fused after amino acid residue 368 of mature CD4 to a sequence from pBR322 which codes for 9 more residues before a translation termination codon. This removes the putative CD4 transmembrane and cytoplasmic domains, which are presumed to anchor CD4 to the cell surface. The plasmid is referred to as pRKCD4T (and produces a protein called CD4T), and was constructed as follows:

pSVeCD4DHFR was digested with HpaII, blunted with Klenow fragment and the four dNTPs, and digested with BstEII. The 382 bp fragment (fragment 17) containing part of the CD4 coding sequence was recovered by gel electrophoresis. pSVeCD4DHFR was digested with EcoRI and BstEII and the 874 bp fragment (fragment 18) recovered. pBR322 was digested with HindIII, blunted with Klenow fragment and the four dNTPs, and digested with EcoRI. Fragment 19 comprising the bulk of the plasmid was isolated and ligated to fragments 17 and 18 and the ligation mixture transformed into E. coli strain 294. The transformed culture was plated on ampicillin media plates and resistant colonies were selected. Plasmid DNA was prepared from transformants and checked by restriction analysis for the presence of the correct fragment. This plasmid is referred to as pCD4Tint.

pRK5 was digested with EcoRI and SmaI and fragment 20 comprising the bulk of the plasmid isolated. pCD4Tint was digested with EcoRI and EcoRV and the 1410 bp fragment containing the CD4 coding sequence to the HpaII site at 1176 bp 3' of the initiating codon and the 154 bp HindIII-EcoRV fragment of pBR322 was recovered (fragment 21). Fragments and 21 were ligated and the ligation mixture was transformed into E. coli strain 294. The transformed culture was plated on ampicillin media plates and resistant colonies were selected. Plasmid DNA was prepared from transformants and checked by restriction analysis for the presence of the correct fragment. This plasmid is referred to as pRKCD4T.

Section 5a

In order to create a secreted form of CD4 which could be purified with an antibody directed to herpes virus type I glycoprotein D, a plasmid was constructed to express a derivative of CD4T in which the region coding for the mature, processed CD4T polypeptide was fused to a sequence coding for the signal peptide and the first 27 residues of the mature type I Herpes Simplex Virus gD glycoprotein. This plasmid is referred to as pRKGDCD4T, and was constructed as follows:

pgDTrunc.DHFR was digested with EcoRI and PvuII and the fragment containing the coding region for the signal peptide and first 27 residues of the mature HSV I gD glycoprotein was isolated (fragment 22). pRKCD4T was digested with EcoRI and BstEII and fragment 23 containing the 3' end of the CD4 coding sequence and the pRK5 region was isolated.

Synthetic oligonucleotides GD (adaptors 1–2, below) containing the coding sequence of CD4 from the codon for the amino terminal residue of mature CD4 to the Rsa site at 121 bp 3' of translation initiation, and containing the sequence CTGCTCGAG at the 5' end of the sense strand were prepared (fragment 24). pRKCD4 was digested with RsaI and BstEII and the 665 bp fragment containing part of the coding region for CD4 was recovered (fragment 25) and ligated to fragment 24. After digestion with BstEII to ensure that only monomeric fragment was present, the 724 bp fragment containing both sequences was recovered by gel electrophoresis (fragment 26).

Fragments 22, 23 and 26 were ligated and the ligation mixture was transformed into E. coli strain 294. The transformed culture was plated on ampicillin media plates and resistant colonies were selected. Plasmid DNA was prepared from transformants and checked by restriction analysis for the presence of the correct fragment. The sequence of several transformants was checked to ensure that the synthetic insert was correct and that reading frame was preserved. This plasmid is referred to as pRKGDCD4T.

These pRK5 derived plasmids preferably were transfected into 293S cells for stable expression according to Muesing, et al. Cell 48:691 (1987), with the exception that in addition to the plasmid of interest a plasmid expressing the neomycin resistance gene pRSV neo (Gorman et al. Science 221:553–555 [1985]) was cotransfected. 293 cells also are used satisfactorily as host cells. 2 days after transfection, the cells were passaged into standard medium (1:1 F12/DME supplemented with L-glutamine, penicillin-streptomycin and 10% FBS) with 0.5 mg/ml G418 (Genticin sulfate; Gibco) for selection of stable cell lines, rather than in media containing methotrexate as shown by Muesing et al. Cells were assayed for production of CD4 or CD4 analogs by radioimmunoprecipitation. Binding studies (section 5c) used conditioned supernatants from these cells in the 1:1 F12/DME medium. Materials used in infectivity assays (section 5b) were obtained as described in section 8 below.

gDCD4 adaptor 1: CTGCTCGAGCAGGGAAA-CAAAGTGGTGCTGGGCAAAAAAGGG-GATACAGTGGAACTGAC (SEQ ID NO: 21)

gDCD4 adaptor 2: pACAGGTCAGTTCCACTGTATC-CCCTTTTTTGCCCAGCAC-CACTTTGTTTCCCTGCTCGA (SEQ ID NO: 22)

Section 5b

The following constitutes a study of the neutralization of HIV-1 infectivity by soluble CD4 analogs. A modification of the neutralization procedure of Robert-Guroff et al., Nature 316:72 (1985) was followed. Equal volumes of inhibitor supernatant and virus (60 microliters) were incubated at 4 degrees C for 1 hour, then the same volume of H9 (Gallo et al., Science 224:500, [1984]) at $5 \times 10^6$/ml was added and incubation continued for 1 hour at 37 degrees C. Following absorption, $2.5 \times 10^5$ cells in 150 microliters were transferred to 2 ml of incubation media. After 4 days at 37 degrees C, the cultures were split 1:2 with fresh media and incubated for an additional 3 days. Cultures were harvested, reverse transcriptase activity was measured (Groopman et al., AIDS Research and Human Retroviruses 3:71 [1987]), and immunofluorescence reactivity with HIV-1 positive serum was determined as described (Poiesz et al., Proc. Acad. Nat. Sci. USA 77:7415 [1980]). Inhibitor supernatants were obtained from confluent plate cultures of 293S/CDT4 cells, 293S/gDCD4T cells or untransfected 293S cells by replacing the growth medium with incubation media and harvesting the supernatants 24 hours later. Inhibitor supernatant replaced part or all of the incubation media during the first three days of culture as indicated in the second column of Table III. Challenge dose of virus was 100 $TCID_{50}$, (Groopman et al., supra) of HIV-1 strain HTLV-IIIB grown in H9 cells assayed in the same system. Incubation media consisted of RPMI 1640 media containing 2 mM L-glutamine, 100 units/ml penicillin, 100 micrograms/ml streptomycin, 2 micrograms/ml polybrene and 20% fetal calf serum (M.A. Bioproducts)e

TABLE III

| Inhibitor supernatant | Dilution of Inhibitor supernatant | Indirect immunofluorescence (% positive cells) | | Reverse transcriptase (cpm/ml × 10⁵) | |
|---|---|---|---|---|---|
| mock-transfected | undil.; 1:4 | 65.3 | 65.5 | 21.8 | 23.9 |
| mock-transfected | undil.; 1:4 | 61.2 | 61.1 | 18.5 | 28.1 |
| CD4T | undil.; 1:4 | 0.4 | 18.0 | 0.11 | 5.94 |
| CD4T | undil.; 1:4 | 0.8 | 16.1 | 0.15 | 3.72 |
| gDCD4T | undil.; 1:4 | 0.4 | 26.8 | 0.14 | 9.92 |
| gDCD4T | undil.; 1:4 | 1.4 | 36.1 | 0.23 | 11.3 |

Both forms of soluble CD4 virtually abolished the growth of HIV-1, when incubated with virus-infected cells without prior dilution (Table III). At a dilution of 1:4 the soluble CD4 preparations were only partially effective in inhibiting virus growth; however, the level of fluorescent-positive cells and reverse transcriptase was still significantly lower than cultures receiving mock-transfected cell supernatants (Table III). Since there was no significant difference in virus growth between diluted and undiluted control supernatants, nor did any of the supernatants affect the growth of uninfected H9 cells (data not shown), soluble 1D4 proteins present in these supernatants were concluded to be responsible for the neutralization of HIV-1 infection of H9 cells.

Section 5c

To determine the affinity constant for interactions between gp120 and CD4 or CD4 variants, saturation binding analysis was carried out with soluble CD4 (supra) and detergent solubilized intact CD4 (Lasky et al. Cell 50:975 [1987]) employing radioiodinated gp120 labeled with lactoperoxidase. Binding reactions consisted of $^{125}$I-gp120 (3 ng to 670 ng, 2.9 nCi/ng) incubated for 1 hour at 0 degrees C with cell lysates containing intact CD4 (Lasky et al., supra) or cell supernatants containing unlabeled CD4T or gDCD4T prepared as described in section 5a. Reactions (0.2 ml) had a final composition of 0.5× McDougal Lysis Buffer (McDLB) (1× McDLB contains 0.5% Nonidet NP-40, 0.2% Na deoxycholate, 0.12 M NaCl, 0.02 M Tris-HCl, pH 8.0) and were performed in duplicate, both in the presence or absence of 50 micrograms of unlabeled purified gp120 (74 fold or greater excess). Following incubation, bound gp120 was quantitated by immunoprecipitation and counted in a gamma counter. For immunoprecipitation, binding reaction solutions were preabsorbed with 5 microliters of normal rabbit serum for one hour at 0° C., and cleared with 40 microliters of Pansorbin (10% w/v, Calbiochem) for 30 minutes at 0 degrees C. Samples were then incubated overnight at 0 degrees C with 2 microliters of normal serum or 5 microliters (0.25 microgram) of OKT4 monoclonal antibody (Ortho) followed by collection of immune complexes with 10 microliters of Pansorbin. Precipitates were washed twice in 1× McDLB and once in water, then eluted by eluting at 100 degrees C for 2 minutes in sample buffer (0.12 M Tris-HCl pH 6.8, 4% SDS, 0.7 M mercaptoethanol, 20% glycerol, and 0.1% bromophenol blue). CD4 molecules were bound saturably by gp120, and yielded a simple mass action binding curve. Supernatants from mock-transfected cells gave a level of specifically bound gp120 less than 1% that found for supernatants containing soluble CD4. Scatchard analysis revealed a single class of binding sites on each molecule, with apparent dissociation constants (Kd) of $1.3 \times 10^{-9}$ M, $0.83 \times 10^{-9}$ M and $0.72 \times 10^{-9}$ M for intact CD4, CD4T and gDCD4T, respectively. The values obtained for CD4-gp120 binding in solution are comparable to the affinity previously measured for gp120 binding to CD4 on whole cells (Kd=$4.0 \times 10^{-9}$ M; Lasky, Cell, supra).

Section 6

In order to produce secreted derivatives of CD4 which are free of extraneous amino acid residues, two plasmids were constructed for expression in 293 cells. The plasmids contain CD4 genes which have been truncated without the addition of extra residues, and are referred to as pRKCD4ΔNla and pRKCD4TP (and produce proteins called CD4ΔNla and CD4TP, respectively), and were constructed as follows:

Fragment 14 containing the CD4 gene with the 195 bp NlaIII restriction fragment deleted was ligated to fragment 16, which is pRK5 digested with EcoRI and BamHI. The ligation mixture was transformed into *E. coli* strain 294, the transformed culture plated on ampicillin media plates and resistant colonies were selected. Plasmid DNA was prepared from transformants and checked by restriction analysis for the presence of the correct fragment. The resulting plasmid is referred to as pRKCD4ΔNla.

Synthetic DNA (5' CGT GAT AGA AGC TTT CTA GAG 3') (SEQ ID NO: 23) was made to attach to the HpaII site at 1176 bp and so that when so attached it would terminate translation after amino acid residue 368 of mature CD4 (fragment 27). The other end of this fragment was designed to ligate to BamHI restriction fragments. pUCCD4 was digested with BstEII and HpaII and the 382 bp fragment containing part of the CD4 gene was recovered (fragment 28). Fragments 27 and 28 were ligated and then digested with BstEII to reduce dimerized fragments to monomers, and the resulting 401 bp fragment was recovered (fragment 29).

pRKCD4 was digested with BstII and BamHI and the fragment comprising the bulk of the plasmid (fragment 30) was isolated and ligated to fragment 29. The ligation mixture was transformed into *E. coli* strain 294, the transformed culture plated on ampicillin media plates and resistant colonies were selected. Plasmid DNA was prepared from transformants and checked by restriction analysis for the presence of the correct fragment. The resulting plasmid is referred to as pRKCD4TP. Both plasmids are transfected into 293 cells to generate stable variant CD4-expressing cell lines as described above.

Section 7

Two plasmids were constructed to direct the expression of secreted CD4 lacking extraneous amino acid residues in CHO cells. These are referred to as pSVeCD4ΔNlaSVDHFR and pSVeCD4TPSVDHFR (and encode proteins having the primary sequence of CD4ΔNla and CD4TP, respectively), and were constructed as follows:

pE348HBV.E400D22 was digested with PvuI and EcoRI and the fragment containing the SV40 early promoter and part of the β-lactamase gene was recovered (fragment 31). pE348HBV.E400D22 was digested with PvuI and BamHI and the large fragment containing the balance of the β-lactamase gene as well as the SV40 early promoter and the DHFR gene was isolated (fragment 32).

Fragments 31 and 32 were ligated together with fragment 14 and transformed into *E. coli* strain 294. The transformed culture was plated on ampicillin media plates and resistant colonies were selected. Plasmid DNA was prepared from transformants and checked by restriction analysis for the presence of the correct fragment. The resulting plasmid is referred to as pSVECD4ΔNlaSVDHFR. This plasmid contains the same DNA fragment encoding the soluble CD4 molecule found in the above-mentioned plasmid pSVeCD4DNlaDHFR (Section 2).

pRKCD4TP was digested with EcoRI and BamHI and the fragment containing the truncated CD4 coding region was isolated and ligated to fragments 31 and 32. The ligation mixture was transformed into *E. coli* strain 294, the transformed culture plated on ampicillin media plates and resistant colonies were selected. Plasmid DNA was prepared from transformants and checked by restriction analysis for the presence of the correct fragment. The resulting plasmid is referred to as pSVeCD4TPSVDHFR. Both of these plasmids are transfected into CHO cells and amplified transfectants selected by methotrexate using conventional procedures.

EXAMPLE 2

Fusions of the V region of the CD4 gene, which is homologous to the variable region of immunoglobulin genes (Maddon et al. 1985, supra), to the constant (C) region of human immunoglobulin κ and γ2 chains are constructed as follows:

Synthetic DNA is made to code for the C region of human κ chain (residues 109–214) based on the sequence published by Morin et al., Proc. Natl. Acad. Sci. 82:7025–7029 (1985), with the addition at the 5' end of the coding strand of the sequence GGGG, which allows this fragment to be ligated to the BspMI site at the end of the putative V-like region of CD4. At the 3' end of the coding region, a translational stop codon is added as well as a sequence which allows this end to be ligated to BamHI restriction fragments. The synthetic DNA is made in 8 fragments, 4 for each strand, 70–90 bases long. These are then allowed to anneal and are ligated prior to isolation on a polyacrylamide gel (fragment 33).

pRKCD4 is digested with EcoRI and BspMI and the 478 bp fragment containing the region coding for the putative V-like domain of CD4 is recovered (fragment 34). Fragments 33 and 34 are ligated together with fragment 16 (from the expression vector pRK5). The ligation mixture is transformed into *E. coli* strain 294, the transformed culture plated on ampicillin media plates and resistant colonies are selected. Plasmid DNA is prepared from transformants and checked by restriction analysis for the presence of the correct fragment. The resulting plasmid is referred to as pRKCD4Cκ.

A plasmid encoding a fusion of the CD4 V-like domain to the human immunoglobulin Cγ2 region is constructed in a similar fashion, and is referred to as pRKCD4Cγ2. Both of these plasmids are transfected into 293 cells, myeloma cells or other competent cells in order to obtain cell lines expressing variant CD4 molecules as described above.

EXAMPLE 3

The gDCD4T secreted by the method of Example 1 was purified from cell culture fluid containing either 10% FBS (fetal bovine serum) or no added FBS. The conditioned cell culture fluid was first concentrated by ultrafiltration, then purified by immunoaffinity chromatography. The immunoaffinity column was produced by coupling murine monoclonal antibody 5B6 (whose epitope is on the HSV-1 gD portion of the gDCD4T molecule) to glyceryl coated controlled pore glass by the method of Roy et al., *J. Chromatography*, 303:225:228 (1984). The concentrated cell culture fluid is applied directly to the column and the contaminating proteins are washed away with neutral pH buffer. The column is then washed with neutral buffer containing tetramethylammonium chloride followed by neutral buffer containing Tween 80. The bound gDCD4T is eluted from the column with buffer at pH3 containing Tween 80 (0.1% w/v) and is neutralized immediately as it is eluted. The eluted neutralized gDCD4T is then concentrated by ultrafiltration and dialyzed/diafiltered to exchange the buffer for a physiological salt solution containing Tween 80 at approximately 0.1% w/v.

If the detergent is not present the gDCD4T forms aggregates as evidenced by the ability of centrifugation at approximately 10,000 × g for 2 minutes to remove the gDCD4T from the solution. Incubation of gDCD4T at 4° C. in 0.1M sodium acetate, 0.5M NaCl and 0.25M Tris at pH 7 together with BSA, Tween 80 or glycerol as candidate stabilizers showed that, in the absence of a stabilizer the gDCD4T gradually aggregated over the space of 12 days to the point where only about 60–70% of the protein was soluble. However, use of 0.1% w/v Tween 80 or 0.5 mg/ml BSA ensured that about 100% or 80%, respectively, of the gDCD4T remained soluble over this period. Surprisingly glycerol was ineffective as a stabilizer and produced results inferior even to the control—at 8 days about 80% of the gDCD4T was aggregated when stored in the presence of glycerol.

EXAMPLE 4

Plasmids were constructed to direct the expression of proteins containing differing lengths of the amino-terminal, extracellular domain of CD4 fused to the constant region of human immunoglobulin γ1. These plasmids are referred to as $pRKCD4_{2\gamma 1}$, $pRKCD4_{e4\gamma 1}$, $pRKCD4_{2\gamma 1}$, $pRKCD4_{e2\gamma 1}$, $pRKCD4_{1\gamma 1}$, and $pRKCD4_{e1\gamma 1}$.

Plasmid $pRKCD4_{4\gamma 1}$ contains the portion of the CD4 gene from the initiation codon to the fusion site after the codon for serine residue 366 of the mature CD4 polypeptide, immediately followed by the sequence coding for the constant region of human immunoglobulin γ1, starting at the codon for serine residue 114 of mature human immunoglobulin γ1 (Kabat et al., Sequences of Proteins or Immunological Interest, National Institute of Health, Bethesda, Md. [1987]).

Plasmid $pRKCD4_{e4\gamma 1}$ contains the portion of the CD4 gene from the initiation codon to the fusion site after the codon for lysine residue 360 of the mature CD4 polypeptide, immediately followed by the sequence coding for the constant region of human immunoglobulin γ1, starting at the codon for serine residue 114 of mature human immunoglobulin γ1 (Kabat et al., supra).

Plasmid $pRKCD4_{2\gamma 1}$ contains the portion of the CD4 gene from the initiation codon to the fusion site after the codon for glutamine residue 180 of the mature CD4 polypeptide, immediately followed by the sequence coding for the constant region of human immunoglobulin γ1, starting at the codon for serine residue 114 of mature human immunoglobulin γ1 (Kabat et al.).

Plasmid $pRKCD4_{e2\gamma 1}$ contains the portion of the CD4 gene from the initiation codon to the fusion site after the codon for leucine residue 177 of the mature CD4 polypeptide, immediately followed by the sequence coding for the constant region of human immunoglobulin γ1, starting at the codon for serine residue 114 of mature human immunoglobulin γ1 (Kabat et al., supra).

Plasmid $pRKCD4_{1\gamma 1}$ contains the portion of the CD4 gene from the initiation codon to the fusion site after the codon for aspartic acid residue 105 of the mature CD4 polypeptide, immediately followed by the sequence coding for the constant region of human immunoglobulin γ1, starting at the codon for serine residue 114 of mature human immunoglobulin γ1 (Kabat et al., supra).

Plasmid $pRKCD4_{e1\gamma 1}$ contains the portion of the CD4 gene from the initiation codon to the fusion site after the codon for leucine residue 100 of the mature CD4 polypeptide, immediately followed by the sequence coding for the constant region of human immunoglobulin γ1, starting at the codon for serine residue 114 of mature human immunoglobulin γ1 (Kabat et al., supra).

Construction of these plasmids required the prior construction of plasmid pRKCD4TP/γ1. It was constructed as follows:

A cDNA clone coding for human immunoglobulin yl was obtained from a human spleen cDNA library (Clontech Laboratories, Inc.) using oligonucleotides based on the published sequence (Ellison et al., "Nucl. Acids Res." 10:4071–4079 [1982]), and an EcoRI-EagI fragment (the EcoRI site was contributed by a linker; see FIGS. 4A, B) containing part of the variable and all of the constant region was obtained. This fragment was blunted with Klenow fragment, and recovered by gel electrophoresis (Fragment al).

Plasmid pRKCD4TP-κκ, encoding a substitutional variant of soluble CD4 (residues 1-368) containing a lysine residue instead of asparagine at position 1 of the mature polypeptide, was constructed from plasmid pRKCD4TP by site-directed mutagenesis. A synthetic oligonucleotide was made as a primer for a mutagenesis reaction to obtain the desired coding sequence. This was synthesized as a 51-mer which contained two silent mutations from the natural sequence in addition to the substitution mutation, and 21 bases on each side of the mutated codons:

5'-CCC TTT TTT GCC CAG CAC CAC CTT CTT GCC CTG AGT GGC TGC TGG GAG GAG -3' (SEQ ID NO: 24)

Plasmid pRKCD4TP was transformed into E. coli strain SR101 and the transformed colonies were plated on ampicillin media plates. Resistant colonies were selected and grown in the presence of m13K07 helper bacteriophage to yield secreted, encapsidated single-stranded templates of pRKCD4TP. The single-stranded plasmid DNA was isolated and used as the template for mutagenesis reactions with the synthetic oligonucleotides described above as primers. The mutagenesis reaction was transformed into E. coli SR101 and the transformed culture plated on ampicillin media plates. Transformants were screened by colony hybridization (ref. Grunstein-Hogness) for the presence of the appropriate sequence, using the following 16 mer as the probe.

5'-C CAC CTT CTT GCC CTG -3' (SEQ ID NO: 25) The hybridization conditions chosen were sufficiently stringent that the probe only detects the correctly fused product. Colonies identified as positive were selected and plasmid DNA was isolated and transformed into E. coli strain SR101. The transformed cultures were plated on ampicillin media plates, and resistant colonies were selected and grown in the presence of m13K07 bacteriophage. Templates were prepared as above and screened by sequencing.

Plasmid pRKCD4TP-κκ was digested with XbaI and treated with Klenow Enzyme, and Fragment a2, containing the linearized plasmid, was recovered by gel electrophoresis, and ligated with fragment al. The ligation mixture was transformed into E. coli strain 294, the transformed culture plated on ampicillin media plates and resistant colonies were selected. Plasmid DNA was prepared from the transformants and checked by restriction analysis for the presence of the correct fragment in the correct orientation (i.e., the immunoglobulin coding region in the same orientation as the CD4 coding region, and at the 3' end of the CD4 coding region). This plasmid is referred to as pRKCD4TP/γ1.

Synthetic oligonucleotides were made as primers for deletional mutagenesis reactions to fuse the appropriate coding sequences of IgG1 and CD4 as described above. These were synthesized as 48-mers comprising 24 nucleotides on each side of the desired fusion site (i.e., corresponding to the COOH-terminal 8 residues of the desired CD4 moiety, and the $NH_2$-terminal 8 residues of the desired immunoglobulin moiety). Plasmid pRKCD4TP/γ1 was transformed into E. coli strain SR101 and the transformed cultures plated on ampicillin media plates. Resistant colonies were selected and grown in the presence of m13K07 helper bacteriophage to yield secreted, encapsidated single-stranded templates of pRKCD4TP/γ1. The single-stranded plasmid DNA was isolated and used as the template for mutagenesis reactions with the synthetic oligonucleotides described above as primers. The mutagenesis reactions were transformed into E. coli SR101 and the transformed culture was plated on ampicillin media plates. Transformants were screened by colony hybridization (ref. Grunstein-Hogness) for the presence of the appropriate fusion site, using 16mers as probes. These 16mers comprise 8 bases on either side of the fusion site, and the hybridization conditions chosen were sufficiently stringent that the probes only detect the correctly fused product. Colonies identified as positive were selected and plasmid DNA was isolated and transformed into E. coli strain SR101.

The transformed cultures were plated on ampicillin media plates, and resistant colonies were selected and grown in the presence of m13KO7 bacteriophage. Templates were prepared as above and screened by sequencing.

The plasmids were transfected into 293 cells using standard procedures and assayed for expression and production as described above.

|  | Expressed | Secreted |
| --- | --- | --- |
| pRKCD4$_{1γ1}$ | + | − |
| pRKCD4$_{e2γ1}$ | + | + |
| pRKCD4$_{2γ1}$ | + | + |
| pRKCD4$_{e4γ1}$ | + | + |
| pRKCD4$_{4γ1}$ | + | + |

Plasmids also were constructed to direct the expression of fusion proteins containing differing lengths of the amino-terminal, extracellular domain of CD4 fused to the truncated portion of the constant region of human immunoglobulin g1, comprising only the hinge region and constant domains $CH_2$ and $CH_3$.

Synthetic oligonucleotides were made as primers for mutagenesis reactions to delete the immunoglobulin sequence from Ser114 to Cys215 inclusive (Kabat et al., Supra). These were synthesized as 48-mers comprising 24 nucleotides on each side of the desired fusion site (i.e., corresponding to the COOH-terminal 8 residues of the desired CD4 moiety, and the $NH_2$-terminal 8 residues of the desired immunoglobulin moiety). Plasmids pRKCD4$_{4γ1}$, pRKCD4$_{2γ1}$ and pRKCD4$_{1γ1}$ were separately transformed into E. coli strain SR101 and the transformed culture was plated on ampicillin media plates. Resistant colonies were selected and grown in the presence of m13KO7 helper bacteriophage to yield secreted, encapsidated single-stranded templates of these plasmids. The single-stranded plasmid DNA was isolated and used as the template for mutagenesis reactions with the synthetic oligonucleotides described above as primers. The mutagenesis reactions were transformed into E. coli SR101 and the transformed culture was plated on ampicillin media plates. Transformants were screened by colony hybridization (Grunstein-Hogness) for the presence of the appropriate fusion site, using 16mers as probes. These 16mers comprise 8 bases on either side of the fusion site, and the hybridization conditions chosen were sufficiently stringent that the probes only detect the correctly fused product. Colonies identified as positive were selected and plasmid DNA was isolated and transformed into *E. coli* strain SR101. The transformed cultures were plated on ampicillin media plates, and resistant colonies were selected and grown in the presence of m13KO7 bacteriophage. Templates were prepared as above and screened by sequencing.

The plasmid derived from plasmid pRKCD4$_{4\gamma1}$ is referred to as pRKCD4$_{4Fc1}$, that derived from plasmid pRKCD4$_{2\gamma1}$ is referred to as pRKCD4$_{2Fc1}$ and that derived from plasmid pRKCD4$_{1\gamma1}$ is referred to as pRKCD4$_{1Fc1}$.

pRKCD4$_{2Fc1}$, pRKCD4$_{2Fc1}$ and pRKCD4$_{4Fc1}$ are cultured in the same fashion as described above and CH1-deleted CD4 immunoadhesons recovered as described elsewhere herein.

Light Chain Fusions

Plasmids were constructed to direct the expression of proteins containing differing lengths of the amino terminal, extracellular domain of CD4 fused to the constant region of human immunoglobulin κ. These plasmids are referred to as pRKCD4$_{4\kappa}$, and pRKCD4$_{e4\kappa}$.

Plasmid pRKCD4$_{4\kappa}$ contains the portion of the CD4 gene from the initiation codon to the fusion site after the codon for serine residue 366 of the mature CD4 polypeptide, immediately followed by the sequence for the constant region of human immunoglobulin κ, starting at the codon for threonine residue 109 of the mature human immunoglobulin κ. (Kabat et al., supra)

Plasmid pRKCD4$_{e4\kappa}$ contains the portion of the CD4 gene from the initiation codon to the fusion site after the codon for lysine residue 360 of the mature CD4 polypeptide, immediately followed by the sequence for the constant region of human immunoglobulin κ, starting at the codon for threonine residue 109 of the mature human immunoglobulin κ. (Kabat et al., supra)

These plasmids were constructed in a manner analogous to plasmids pRKCD4$_{4\gamma1}$ and pRKCD4$_{e4\gamma1}$ described above, with the following exception:

The human immunoglobulin κ coding sequence (FIG. 5) was obtained from a human spleen cDNA library (Clontech Laboratories, Inc.) using oligonucleotides based on the published sequence (Hieter, P. A. et al., Cell 22:197–207 [1980]) and an EcoRI-BspMI fragment containing part of the variable region and the entire constant region was obtained (see FIG. 5). This fragment was blunted with Klenow fragment and the four dNTPs. This fragment was used instead of fragment al, and was used to construct plasmid pRKCD4TP/hκ.

Expression in CHO Cells

Plasmids were or are constructed to direct the expression of the immunoadhesons described above in CHO cells. These are referred to as pSVeCD4$_{4\gamma1}$SVDHFR, pSVeCD4$_{2\gamma1}$SVDHFR, pSVeCD4$_{1\gamma1}$SVDHFR, pSVeCD4$_{e4\gamma1}$SVDHFR, pSVeCD4$_{e2\gamma1}$SVDHFR, pSVeCD4$_{e1\gamma1}$SVDHFR, pSVeCD4$_{4Fc1}$SVDHFR, pSVeCD4$_{2Fc1}$SVDHFR, pSVeCD4$_{1Fc1}$SVDHFR, pSVeCD4$_{4\kappa}$SVDHFR and pSVeCD4$_{2\kappa}$SVDHFR.

Fragment 31 was prepared as described above. Fragment 32a was prepared by digesting plasmid pE348HBV.E400 D22 with BamHI, blunting with Klenow fragment and the four dNTPs, then digesting with PvuI and isolating the large fragment containing the balance of the β-lactamase gene and the SV40 early promoter and the DHFR gene. Plasmids pRKCD4$_{4\gamma1}$, pRKCD4$_{2\gamma1}$, pRKCD4$_{1\gamma1}$, pRKCD4$_{e4\gamma1}$, pRKCD4$_{e2\gamma1}$, pRKCD4$_{e1\gamma1}$, pRKCD4$_{4Fc1}$, pRKCD4$_{2Fc1}$, pRKCD4$_{1Fc1}$, pRKCD4$_{4\kappa}$, and pRKCD4$_{e4\kappa}$ were separately digested with HindIII, blunted with Klenow fragment and the four dNTPs, then digested with EcoRI and the fragments encoding the CD4-Ig fusion protein were isolated. The resulting DNA fragments were ligated together with fragments 31 and 32a and transformed into *E. coli* strain 294. Colonies were selected and checked for the presence of the correct plasmid as above, then transfected into CHO cells and amplified by methotrexate selection using conventional procedures.

EXAMPLE 5

Culture, Purification and Formulation of CD4 Variants

Plasmids encoding soluble CD4 adhesons such as CD4T, CD4TP, or soluble CD4 immunoadhesons were calcium phosphate transfected into CHO-DP7 (a proinsulin-transformed autocrine host cell derived from CHO; U.S. Ser. No. 97,472, supra) and the transformants grown in selective medium (1:1 HAM F12/DMEM GHT-containing 1–10% diafiltered or dialyzed bovine serum). Other suitable host cells are CHO cells or 293S human embryonic kidney cells. The transformants were amplified by methotrexate selection in the same medium but containing 500 nm methotrexate. A subclone capable of secreting CD4TP, CD4tp 500 b, was selected. CD4tp 500 b is cultured in a DMEM/HAM F12 medium at about 37° C. until CD4TP accumulates in the culture, after which the medium is separated from the cells and insoluble matter by centrifuging.

Culture fluid from CD4TP transformants was concentrated and diafiltered to lower the ionic strength. The concentrate was passed through a large volume of Q-Sepharose anion exchange resin (previously equilibrated with mM NaCl, pH 8.5) in order to adsorb contaminants from the culture fluid. The isoelectric point of CD4TP is about 9.5, thus making it possible to discriminate between truncated forms of CD4 and most contaminants by alternate adsorption, respectively, on a cation exchange resin such as carboxymethyl or sulfonyl Sepharose, and an anion exchange resin such as quaternary ammonium Sepharose. In addition, since highly electropositive domains are present in the extracellular segment of CD4, any CD4-containing variant is purified in the same fashion as CD4TP. The unadsorbed culture fluid from the anion exchange resin step was then passed through a cation exchange resin (previously equilibrated with 25 mM NaCl at pH 8.5) whereby CD4TP was adsorbed to the resin. The CD4TP was eluted with a NaCl gradient at pH 8.5, this CD4 variant eluting at about 0.2 M NaCl. Ammonium sulfate was added to the eluate to a concentration of 1.7M and the solution passed through a column of hydrophobic interaction chromatography resin (phenyl or butyl Sepharose). The CD4TP was eluted from the hydrophobic interaction column with a gradient of ammonium sulfate, the CD4TP emerging at about 0.7M ammonium sulfate. The eluate was concentrated and buffer exchanged on a G-25 column using phosphate buffered saline containing 0.02% (w/v) Tween 20 or Tween 80. The CD4TP was soluble and stable in this solution, which was sterile filtered and filled into vials as an aqueous formulation. Other polymeric nonionic surfactants are suitably used with the CD4 formulations, including Pluronic block copolymers or polyethylene glycol.

It is also possible to employ immunoaffinity purification of soluble CD4 wherein the CD4 is adsorbed onto an immobilized antibody against CD4. This method suffers from the disadvantage that elution of the soluble CD4 under acidic conditions leads to protein aggregation that is only thoroughly ameliorated at relatively higher levels of surfactant. The foregoing procedure permits the use of much lower quantities of surfactant, about from 0.01 to 0.10% (w/v) surfactant.

The procedure followed for the purification of CD4 fusions with immunoglobulin heavy chain was to concentrate recombinant supernatants by ultrafiltration and thereafter adsorb the fusion onto resin-immobilized Staphylococcal protein A. The fusion was eluted with 0.1M citrate buffer pH 3 with no salt or detergent. This preparation is buffered into Tris buffer at pH 7.5. The immunoglobulin fusions with CD4 V1–V4 optionally are further purified by the procedure described above for unfused CD4 variants. CD4 immunoglobulin fusions with CD4 V1–V2 also may be purified by the procedure above, except that it is not expected that the isoelectric point of this class of molecules will be as alkaline as that of species containing all four V regions of CD4.

EXAMPLE 6

The characteristics of several adheson variants were determined. As shown in Table IV the immunoadhesons $CD4_{4\gamma 1}$ and $CD4_{2\gamma 1}$ show improved plasma half-life in rabbits, coupled with high-affinity gp120 binding and an affinity for Fcγ receptor (determined with U937 cells) that is comparable to that of bulk human IgG1.

TABLE IV

|  | gp120 KD (nM)[19Ø] | FcγR KD (nM)[+] | Plasma Half-life[++] In Rabbits (Hrs.) |
|---|---|---|---|
| CD4T[S17] | 2.3 ± 0.4 | Not detected | 0.25 |
| $CD4_{4\gamma 1}$ | 1.2 ± 0.1 | 2.83 ± 0.25 | 6.4. |
| $CD4_{2\gamma 1}$ | 1.4 ± 0.1 | 3.01 ± 0.68 | 40.6 |
| human IgG1 | ND** | 3.52 ± 0.5 | 21 days* |

*determined in humans

+determined by the method of Anderson et al., "J. Immunol." 125:2735–2741 (1980).

determined by the method of Smith et al., "Science" 238:1704–07 (1987).

§residues 1–368 only

++The adheson variant was injected intravenously into rabbits and samples of blood were collected periodically and assayed for the presence of the adheson variant.

**Not done.

---

We claim:

1. Nucleic acid encoding an immunoadheson in which a polypeptide comprising an adheson variable region is fused at its C-terminus to the N-terminus of a polypeptide comprising a constant region of an immunoglobulin.

2. The nucleic acid according to claim 1 wherein the immunoglobulin constant region is selected from the group consisting of IgG-1, IgG-2, IgG-3, IgG-4, IgA, IgE, IgD, and IgM.

3. The nucleic acid according to claim 2 wherein the immunoglobulin constant region is selected from the group consisting of IgG-1 and IgG-3.

4. The nucleic acid according to claim 2 wherein the immunoglobulin constant region is selected from the group consisting of IgA and IgM.

5. The nucleic acid of claim 1 wherein the immunoglobulin constant region is the constant region of the immunoglobulin light chain.

6. The nucleic acid of claim 1 wherein the immunoglobulin constant region is the constant region of an immunoglobulin heavy chain.

7. The nucleic acid of claim 1 wherein the adheson variable region is the variable region of an adheson selected from the group consisting of CD1, CD2, CD4, CD8, CD28, the γ, δ, or ε chains of CD3, an intercellular adhesion molecule, LFA-3 and the high affinity IgE receptor.

8. The nucleic acid of claim 7 wherein the adheson variable region is a variable region of human CD4.

9. The nucleic acid of claim 8 wherein the human CD4 variable region comprises the V1 and V2 domains of human CD4.

10. The nucleic acid of claim 9 wherein the human CD4 variable region comprises the V1, V2, V3 and V4 domains of human CD4.

11. The nucleic acid of claim 9 wherein the human CD4 variable region comprises the sequence Asn-Lys-Val-Val-Leu-Gly-Lys-Lys.

12. The nucleic acid of claim 8 wherein the human CD4 variable region comprises the amino acid sequence extending from residues 24 to 117 of the precursor of human CD4 in which the initiating Met is 1.

13. The nucleic acid of claim 8 further comprising a nucleic acid encoding a signal sequence heterologous to the naturally occurring human CD4 gene.

14. The nucleic acid of claim 1 further comprising a nucleic acid encoding a signal sequence heterologous to the signal sequence naturally associated with the adheson variable region.

15. A recombinant host cell comprising the nucleic acid of claim 1.

16. The recombinant host cell of claim 15 further comprising a nucleic acid encoding a companion immunoglobulin heavy chain-light chain pair bearing a $V_L V_H$ antibody combining site capable of binding to a predetermined antigen.

17. The host cell according to claim 16 wherein the $V_L V_H$ antibody combining site is from an anti-ricin antibody.

18. The host cell of claim 16 which is a mammalian cell.

19. A method of preparing an immunoadheson comprising transfecting a host cell with the nucleic acid of claim 1 and thereafter culturing the host under conditions suitable for the expression of the immunoadheson.

20. The method of claim 18 wherein the immunoadheson is recovered from the host cell culture.

21. A replicable vector comprising the nucleic acid of claim 1.

22. The nucleic acid of claim 1 wherein the adheson variable region is fused at its C-terminus to the N-terminus of the constant region of the immunoglobulin.

23. The nucleic acid of claim 22 wherein the immunoglobulin constant region is the constant region of an immunoglobulin heavy chain.

24. The nucleic acid of claim 23 wherein the immunoglobulin constant region is the constant region of an IgG.

25. The nucleic acid of claim 23 wherein the adheson variable region is the variable region of an adheson selected from the group consisting of CD1, CD2, CD4, CD8, CD28, the $\gamma$, $\delta$, or $\epsilon$ chains of CD3, an intercellular adhesion molecule, LFA-3 and the high affinity IgE receptor.

26. The nucleic acid of claim 25 wherein the adheson is LFA-3.

27. The nucleic acid of claim 22 further comprising a nucleic acid encoding a signal sequence heterologous to the signal sequence naturally associated with the adheson variable region.

28. A recombinant host cell comprising the nucleic acid of claim 22.

29. The host cell of claim 28 which is a mammalian cell.

30. A method of preparing an immunoadheson comprising transfecting a host cell with the nucleic acid of claim 22 and thereafter culturing the host under conditions suitable for the expression of the immunoadheson.

* * * * *

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 402 amino acids
      (B) TYPE: amino acid
      (D) TOPOLOGY: linear (xi) SEQUENCE DESCRIPTION: SEQ ID NO:1:

```
Met Asn Arg Gly Val Pro Phe Arg His Leu Leu Leu Val Leu Gln
 1               5                  10                  15

Leu Ala Leu Leu Pro Ala Ala Thr Gln Gly Asn Lys Val Val Leu
                20                  25                  30

Gly Lys Lys Gly Asp Thr Val Glu Leu Thr Cys Thr Ala Ser Gln
                35                  40                  45

Lys Lys Ser Ile Gln Phe His Trp Lys Asn Ser Asn Gln Ile Lys
                50                  55                  60

Ile Leu Gly Asn Gln Gly Ser Phe Leu Thr Lys Gly Pro Ser Lys
                65                  70                  75

Leu Asn Asp Arg Ala Asp Ser Arg Arg Ser Leu Trp Asp Gln Gly
                80                  85                  90

Asn Phe Pro Leu Ile Ile Lys Asn Leu Lys Ile Glu Asp Ser Asp
                95                 100                 105

Thr Tyr Ile Cys Glu Val Glu Asp Gln Lys Glu Glu Val Gln Leu
               110                 115                 120

Leu Val Phe Gly Leu Thr Ala Asn Ser Asp Thr His Leu Leu Gln
               125                 130                 135

Gly Gln Ser Leu Thr Leu Thr Leu Glu Ser Pro Pro Gly Ser Ser
               140                 145                 150
```

-continued

```
Pro Ser Val Gln Cys Arg Ser Pro Arg Gly Lys Asn Ile Gln Gly
            155                 160                 165

Gly Lys Thr Leu Ser Val Ser Gln Leu Glu Leu Gln Asp Ser Gly
            170                 175                 180

Thr Trp Thr Cys Thr Val Leu Gln Asn Gln Lys Lys Val Glu Phe
            185                 190                 195

Lys Ile Asp Ile Val Val Leu Ala Phe Gln Lys Ala Ser Ser Ile
            200                 205                 210

Val Tyr Lys Lys Glu Gly Glu Gln Val Glu Phe Ser Phe Pro Leu
            215                 220                 225

Ala Phe Thr Val Glu Lys Leu Thr Gly Ser Gly Glu Leu Trp Trp
            230                 235                 240

Gln Ala Glu Arg Ala Ser Ser Ser Lys Ser Trp Ile Thr Phe Asp
            245                 250                 255

Leu Lys Asn Lys Glu Val Ser Val Lys Arg Val Thr Gln Asp Pro
            260                 265                 270

Lys Leu Gln Met Gly Lys Lys Leu Pro Leu His Leu Thr Leu Pro
            275                 280                 285

Gln Ala Leu Pro Gln Tyr Ala Gly Ser Gly Asn Leu Thr Leu Ala
            290                 295                 300

Leu Glu Ala Lys Thr Gly Lys Leu His Gln Glu Val Asn Leu Val
            305                 310                 315

Val Met Arg Ala Thr Gln Leu Gln Lys Asn Leu Thr Cys Glu Val
            320                 325                 330

Trp Gly Pro Thr Ser Pro Lys Leu Met Leu Ser Leu Lys Leu Glu
            335                 340                 345

Asn Lys Glu Ala Lys Val Ser Lys Arg Glu Lys Ala Val Trp Val
            350                 355                 360

Leu Asn Pro Glu Ala Gly Met Trp Gln Cys Leu Leu Ser Asp Ser
            365                 370                 375

Gly Gln Val Leu Leu Glu Ser Asn Ile Lys Val Leu Pro Thr Trp
            380                 385                 390

Ser Thr Pro Ser Phe Asn Ala Val Val Tyr His Ser
            395                 400     402
```

(2) INFORMATION FOR SEQ ID NO:2:

(i) SEQUENCE CHARACTERISTICS:
        (A) LENGTH: 1416 bases
        (B) TYPE: nucleic acid
        (C) STRANDEDNESS: single
        (D) TOPOLOGY: linear (xi) SEQUENCE DESCRIPTION: SEQ ID NO:2:

```
AATTCAAGCC CAGAGCCCTG CCATTTCTGT GGGCTCAGGT CCCTACTGCT         50

CAGCCCCTTC CTCCCTCGGC AAGGCCACAA TGAACCGGGG AGTCCCTTTT        100

AGGCACTTGC TTCTGGTGCT GCAACTGGCG CTCCTCCCAG CAGCCACTCA        150

GGGAAACAAA GTGGTGCTGG GCAAAAAAGG GGATACAGTG GAACTGACCT        200

GTACAGCTTC CCAGAAGAAG AGCATACAAT TCCACTGGAA AAACTCCAAC        250

CAGATAAAGA TTCTGGGAAA TCAGGGCTCC TTCTTAACTA AAGGTCCATC        300

CAAGCTGAAT GATCGCGCTG ACTCAAGAAG AAGCCTTTGG GACCAAGGAA        350

ACTTTCCCCT GATCATCAAG AATCTTAAGA TAGAAGACTC AGATACTTAC        400
```

```
ATCTGTGAAG TGGAGGACCA GAAGGAGGAG GTGCAATTGC TAGTGTTCGG        450

ATTGACTGCC AACTCTGACA CCCACCTGCT TCAGGGGCAG AGCCTGACCC        500

TGACCTTGGA GAGCCCCCCT GGTAGTAGCC CCTCAGTGCA ATGTAGGAGT        550

CCAAGGGGTA AAACATACA GGGGGGGAAG ACCCTCTCCG TGTCTCAGCT         600

GGAGCTCCAG GATAGTGGCA CCTGGACATG CACTGTCTTG CAGAACCAGA        650

AGAAGGTGGA GTTCAAAATA GACATCGTGG TGCTAGCTTT CCAGAAGGCC        700

TCCAGCATAG TCTATAAGAA AGAGGGGAA CAGGTGGAGT TCTCCTTCCC         750

ACTCGCCTTT ACAGTTGAAA AGCTGACGGG CAGTGGCGAG CTGTGGTGGC        800

AGGCGGAGAG GGCTTCCTCC TCCAAGTCTT GGATCACCTT TGACCTGAAG        850

AACAAGGAAG TGTCTGTAAA ACGGGTTACC CAGGACCCTA AGCTCCAGAT        900

GGGCAAGAAG CTCCCGCTCC ACCTCACCCT GCCCCAGGCC TTGCCTCAGT        950

ATGCTGGCTC TGGAAACCTC ACCCTGGCCC TTGAAGCGAA AACAGGAAAG       1000

TTGCATCAGG AAGTGAACCT GGTGGTGATG AGAGCCACTC AGCTCCAGAA       1050

AAATTTGACC TGTGAGGTGT GGGGACCCAC CTCCCCTAAG CTGATGCTGA       1100

GTTTGAAACT GGAGAACAAG GAGGCAAAGG TCTCGAAGCG GGAGAAGGCG       1150

GTGTGGGTGC TGAACCCTGA GGCGGGGATG TGGCAGTGTC TGCTGAGTGA       1200

CTCGGGACAG GTCCTGCTGG AATCCAACAT CAAGGTTCTG CCCACATGGT       1250

CCACCCCGAG CTTTAATGCG GTAGTTTATC ACAGTTAAAT TGCTAACGCA       1300

GTCAGGCACC GTGTATGAAA TCTAACAATG CGCTCATCGT CATCCTCGGC       1350

ACCGTCACCC TGGATGCTGT AGGCATAGGC TTGGTTATGC CGGTACTGCC       1400

GGGCCTCTTG CGGGAT                                            1416

(2) INFORMATION FOR SEQ ID NO:3:

(i) SEQUENCE CHARACTERISTICS:
        (A) LENGTH: 1416 bases
        (B) TYPE: nucleic acid
        (C) STRANDEDNESS: single
        (D) TOPOLOGY: linear (xi) SEQUENCE DESCRIPTION: SEQ ID NO:3:

TTAAGTTCGG GTCTCGGGAC GGTAAAGACA CCCGAGTCCA GGGATGACGA         50

GTCGGGAAG GAGGGAGCCG TTCCGGTGTT ACTTGGCCCC TCAGGGAAAA         100

TCCGTGAACG AAGACCACGA CGTTGACCGC GAGGAGGGTC GTCGGTGAGT        150

CCCTTTGTTT CACCACGACC CGTTTTTTCC CCTATGTCAC CTTGACTGGA        200

CATGTCGAAG GGTCTTCTTC TCGTATGTTA AGGTGACCTT TTTGAGGTTG        250

GTCTATTTCT AAGACCCTTT AGTCCCGAGG AAGAATTGAT TTCCAGGTAG        300

GTTCGACTTA CTAGCGCGAC TGAGTTCTTC TTCGGAAACC CTGGTTCCTT        350

TGAAAGGGGA CTAGTAGTTC TTAGAATTCT ATCTTCTGAG TCTATGAATG        400

TAGACACTTC ACCTCCTGGT CTTCCTCCTC CACGTTAACG ATCACAAGCC        450

TAACTGACGG TTGAGACTGT GGGTGGACGA AGTCCCCGTC TCGGACTGGG        500

ACTGGAACCT CTCGGGGGA CCATCATCGG GGAGTCACGT TACATCCTCA         550

GGTTCCCCAT TTTTGTATGT CCCCCCCTTC TGGGAGAGGC ACAGAGTCGA        600

CCTCGAGGTC CTATCACCGT GGACCTGTAC GTGACAGAAC GTCTTGGTCT        650
```

```
TCTTCCACCT CAAGTTTTAT CTGTAGCACC ACGATCGAAA GGTCTTCCGG         700

AGGTCGTATC AGATATTCTT TCTCCCCCTT GTCCACCTCA AGAGGAAGGG         750

TGAGCGGAAA TGTCAACTTT TCGACTGCCC GTCACCGCTC GACACCACCG         800

TCCGCCTCTC CCGAAGGAGG AGGTTCAGAA CCTAGTGGAA ACTGGACTTC         850

TTGTTCCTTC ACAGACATTT TGCCCAATGG GTCCTGGGAT TCGAGGTCTA         900

CCCGTTCTTC GAGGGCGAGG TGGAGTGGGA CGGGGTCCGG AACGGAGTCA         950

TACGACCGAG ACCTTTGGAG TGGGACCGGG AACTTCGCTT TTGTCCTTTC        1000

AACGTAGTCC TTCACTTGGA CCACCACTAC TCTCGGTGAG TCGAGGTCTT        1050

TTTAAACTGG ACACTCCACA CCCCTGGGTG GAGGGGATTC GACTACGACT        1100

CAAACTTTGA CCTCTTGTTC CTCCGTTTCC AGAGCTTCGC CCTCTTCCGC        1150

CACACCCACG ACTTGGGACT CCGCCCCTAC ACCGTCACAG ACGACTCACT        1200

GAGCCCTGTC CAGGACGACC TTAGGTTGTA GTTCCAAGAC GGGTGTACCA        1250

GGTGGGGCTC GAAATTACGC CATCAAATAG TGTCAATTTA ACGATTGCGT        1300

CAGTCCGTGG CACATACTTT AGATTGTTAC GCGAGTAGCA GTAGGAGCCG        1350

TGGCAGTGGG ACCTACGACA TCCGTATCCG AACCAATACG GCCATGACGG        1400

CCCGGAGAAC GCCCTA                                             1416

(2) INFORMATION FOR SEQ ID NO:4:

(i) SEQUENCE CHARACTERISTICS:
        (A) LENGTH: 434 amino acids
        (B) TYPE: amino acid
        (D) TOPOLOGY: linear (xi) SEQUENCE DESCRIPTION: SEQ ID NO:4:

Met Gly Gly Thr Ala Ala Arg Leu Gly Ala Val Ile Leu Phe Val
 1               5                  10                  15

Val Ile Val Gly Leu His Gly Val Arg Gly Lys Tyr Ala Leu Ala
                20                  25                  30

Asp Ala Ser Leu Lys Met Ala Asp Pro Asn Arg Phe Arg Gly Lys
                35                  40                  45

Asp Leu Pro Val Leu Asp Gln Leu Leu Glu Gln Gly Asn Lys Val
                50                  55                  60

Val Leu Gly Lys Lys Gly Asp Thr Val Glu Leu Thr Cys Thr Ala
                65                  70                  75

Ser Gln Lys Lys Ser Ile Gln Phe His Trp Lys Asn Ser Asn Gln
                80                  85                  90

Ile Lys Ile Leu Gly Asn Gln Gly Ser Phe Leu Thr Lys Gly Pro
                95                 100                 105

Ser Lys Leu Asn Asp Arg Ala Asp Ser Arg Arg Ser Leu Trp Asp
               110                 115                 120

Gln Gly Asn Phe Pro Leu Ile Ile Lys Asn Leu Lys Ile Glu Asp
               125                 130                 135

Ser Asp Thr Tyr Ile Cys Glu Val Glu Asp Gln Lys Glu Glu Val
               140                 145                 150

Gln Leu Leu Val Phe Gly Leu Thr Ala Asn Ser Asp Thr His Leu
               155                 160                 165

Leu Gln Gly Gln Ser Leu Thr Leu Thr Leu Glu Ser Pro Pro Gly
               170                 175                 180

Ser Ser Pro Ser Val Gln Cys Arg Ser Pro Arg Gly Lys Asn Ile
```

```
                      185                 190                 195
Gln Gly Gly Lys Thr Leu Ser Val Ser Gln Leu Glu Leu Gln Asp
                200                 205                 210
Ser Gly Thr Trp Thr Cys Thr Val Leu Gln Asn Gln Lys Lys Val
                215                 220                 225
Glu Phe Lys Ile Asp Ile Val Val Leu Ala Phe Gln Lys Ala Ser
                230                 235                 240
Ser Ile Val Tyr Lys Lys Glu Gly Glu Gln Val Glu Phe Ser Phe
                245                 250                 255
Pro Leu Ala Phe Thr Val Glu Lys Leu Thr Gly Ser Gly Glu Leu
                260                 265                 270
Trp Trp Gln Ala Glu Arg Ala Ser Ser Lys Ser Trp Ile Thr
                275                 280                 285
Phe Asp Leu Lys Asn Lys Glu Val Ser Val Lys Arg Val Thr Gln
                290                 295                 300
Asp Pro Lys Leu Gln Met Gly Lys Lys Leu Pro Leu His Leu Thr
                305                 310                 315
Leu Pro Gln Ala Leu Pro Gln Tyr Ala Gly Ser Gly Asn Leu Thr
                320                 325                 330
Leu Ala Leu Glu Ala Lys Thr Gly Lys Leu His Gln Glu Val Asn
                335                 340                 345
Leu Val Val Met Arg Ala Thr Gln Leu Gln Lys Asn Leu Thr Cys
                350                 355                 360
Glu Val Trp Gly Pro Thr Ser Pro Lys Leu Met Leu Ser Leu Lys
                365                 370                 375
Leu Glu Asn Lys Glu Ala Lys Val Ser Lys Arg Glu Lys Ala Val
                380                 385                 390
Trp Val Leu Asn Pro Glu Ala Gly Met Trp Gln Cys Leu Leu Ser
                395                 400                 405
Asp Ser Gly Gln Val Leu Leu Glu Ser Asn Ile Lys Val Leu Pro
                410                 415                 420
Thr Trp Ser Thr Pro Ser Phe Asn Ala Val Val Tyr His Ser
                425                 430                 434

(2) INFORMATION FOR SEQ ID NO:5:

(i) SEQUENCE CHARACTERISTICS:
        (A) LENGTH: 1508 bases
        (B) TYPE: nucleic acid
        (C) STRANDEDNESS: single
        (D) TOPOLOGY: linear (xi) SEQUENCE DESCRIPTION: SEQ ID NO:5:

AAGCTTCAGC GCGAACGACC AACTACCCCG ATCATCAGTT ATCCTTAAGG         50

TCTCTTTTGT GTGGTGCGTT CCGGTATGGG GGGGACTGCC GCCAGGTTGG         100

GGGCCGTGAT TTTGTTTGTC GTCATAGTGG GCCTCCATGG GGTCCGCGGC         150

AAATATGCCT TGGCGGATGC CTCTCTCAAG ATGGCCGACC CCAATCGATT         200

TCGCGGCAAA GACCTTCCGG TCCTGGACCA GCTGCTCGAG CAGGGAAACA         250

AAGTGGTGCT GGGCAAAAAA GGGGATACAG TGGAACTGAC CTGTACAGCT         300

TCCCAGAAGA AGAGCATACA ATTCCACTGG AAAAACTCCA ACCAGATAAA         350

GATTCTGGGA AATCAGGGCT CCTTCTTAAC TAAAGGTCCA TCCAAGCTGA         400

ATGATCGCGC TGACTCAAGA GAAGCCTTT GGGACCAAGG AAACTTTCCC          450
```

```
CTGATCATCA AGAATCTTAA GATAGAAGAC TCAGATACTT ACATCTGTGA      500

AGTGGAGGAC CAGAAGGAGG AGGTGCAATT GCTAGTGTTC GGATTGACTG      550

CCAACTCTGA CACCCACCTG CTTCAGGGGC AGAGCCTGAC CCTGACCTTG      600

GAGAGCCCCC CTGGTAGTAG CCCCTCAGTG CAATGTAGGA GTCCAAGGGG      650

TAAAAACATA CAGGGGGGGA AGACCCTCTC CGTGTCTCAG CTGGAGCTCC      700

AGGATAGTGG CACCTGGACA TGCACTGTCT TGCAGAACCA GAAGAAGGTG      750

GAGTTCAAAA TAGACATCGT GGTGCTAGCT TTCCAGAAGG CCTCCAGCAT      800

AGTCTATAAG AAAGAGGGGG AACAGGTGGA GTTCTCCTTC CCACTCGCCT      850

TTACAGTTGA AAAGCTGACG GGCAGTGGCG AGCTGTGGTG GCAGGCGGAG      900

AGGGCTTCCT CCTCCAAGTC TTGGATCACC TTTGACCTGA AGAACAAGGA      950

AGTGTCTGTA AAACGGGTTA CCCAGGACCC TAAGCTCCAG ATGGGCAAGA      1000

AGCTCCCGCT CCACCTCACC CTGCCCCAGG CCTTGCCTCA GTATGCTGGC      1050

TCTGGAAACC TCACCCTGGC CCTTGAAGCG AAAACAGGAA AGTTGCATCA      1100

GGAAGTGAAC CTGGTGGTGA TGAGAGCCAC TCAGCTCCAG AAAAATTTGA      1150

CCTGTCAGGT GTGGGACCC ACCTCCCCTA AGCTGATGCT GAGTTTGAAA       1200

CTGGAGAACA AGGAGGCAAA GGTCTCGAAG CGGGAGAAGG CGGTGTGGGT      1250

GCTGAACCCT GAGGCGGGGA TGTGGCAGTG TCTGCTGAGT GACTCGGGAC      1300

AGGTCCTGCT GGAATCCAAC ATCAAGGTTC TGCCCACATG GTCCACCCCG      1350

AGCTTTAATG CGGTAGTTTA TCACAGTTAA ATTGCTAACG CAGTCAGGCA      1400

CCGTGTATGA AATCTAACAA TGCGCTCATC GTCATCCTCG GCACCGTCAC      1450

CCTGGATGCT GTAGGCATAG GCTTGGTTAT GCCGGTACTG CCGGGCCTCT      1500

TGCGGGAT                                                    1508

(2) INFORMATION FOR SEQ ID NO:6:

(i) SEQUENCE CHARACTERISTICS:
        (A) LENGTH: 1508 bases
        (B) TYPE: nucleic acid
        (C) STRANDEDNESS: single
        (D) TOPOLOGY: linear (xi) SEQUENCE DESCRIPTION: SEQ ID NO:6:

TTCGAAGTCG CGCTTGCTGG TTGATGGGGC TAGTAGTCAA TAGGAATTCC       50

AGAGAAAACA CACCACGCAA GGCCATACCC CCCCTGACGG CGGTCCAACC      100

CCCGGCACTA AAACAAACAG CAGTATCACC CGGAGGTACC CCAGGCGCCG     150

TTTATACGGA ACCGCCTACG GAGAGAGTTC TACCGGCTGG GGTTAGCTAA     200

AGCGCCGTTT CTGGAAGGCC AGGACCTGGT CGACGAGCTC GTCCCTTTGT     250

TTCACCACGA CCCGTTTTTT CCCCTATGTC ACCTTGACTG GACATGTCGA     300

AGGGTCTTCT TCTCGTATGT TAAGGTGACC TTTTTGAGGT TGGTCTATTT     350

CTAAGACCCT TTAGTCCCGA GGAAGAATTG ATTTCCAGGT AGGTTCGACT     400

TACTAGCGCG ACTGAGTTCT TCTTCGGAAA CCCTGGTTCC TTTGAAAGGG     450

GACTAGTAGT TCTTAGAATT CTATCTTCTG AGTCTATGAA TGTAGACACT     500

TCACCTCCTG GTCTTCCTCC TCCACGTTAA CGATCACAAG CCTAACTGAC     550

GGTTGAGACT GTGGGTGGAC GAAGTCCCCG TCTCGGACTG GGACTGGAAC     600
```

-continued

```
CTCTCGGGGG GACCATCATC GGGGAGTCAC GTTACATCCT CAGGTTCCCC         650

ATTTTTGTAT GTCCCCCCCT TCTGGGAGAG GCACAGAGTC GACCTCGAGG         700

TCCTATCACC GTGGACCTGT ACGTGACAGA ACGTCTTGGT CTTCTTCCAC         750

CTCAAGTTTT ATCTGTAGCA CCACGATCGA AAGGTCTTCC GGAGGTCGTA         800

TCAGATATTC TTTCTCCCCC TTGTCCACCT CAAGAGGAAG GGTGAGCGGA         850

AATGTCAACT TTTCGACTGC CCGTCACCGC TCGACACCAC CGTCCGCCTC         900

TCCCGAAGGA GGAGGTTCAG AACCTAGTGG AAACTGGACT TCTTGTTCCT         950

TCACAGACAT TTTGCCCAAT GGGTCCTGGG ATTCGAGGTC TACCCGTTCT        1000

TCGAGGGCGA GGTGGAGTGG GACGGGGTCC GGAACGGAGT CATACGACCG        1050

AGACCTTTGG AGTGGGACCG GGAACTTCGC TTTTGTCCTT TCAACGTAGT        1100

CCTTCACTTG GACCACCACT ACTCTCGGTG AGTCGAGGTC TTTTTAAACT        1150

GGACACTCCA CACCCCTGGG TGGAGGGGAT TCGACTACGA CTCAAACTTT        1200

GACCTCTTGT TCCTCCGTTT CCAGAGCTTC GCCCTCTTCC GCCACACCCA        1250

CGACTTGGGA CTCCGCCCCT ACACCGTCAC AGACGACTCA CTGAGCCCTG        1300

TCCAGGACGA CCTTAGGTTG TAGTTCCAAG ACGGGTGTAC CAGGTGGGGC        1350

TCGAAATTAC GCCATCAAAT AGTGTCAATT TAACGATTGC GTCAGTCCGT        1400

GGCACATACT TTAGATTGTT ACGCGAGTAG CAGTAGGAGC CGTGGCAGTG        1450

GGACCTACGA CATCCGTATC CGAACCAATA CGGCCATGAC GGCCCGGAGA        1500

ACGCCCTA                                                     1508
```

(2) INFORMATION FOR SEQ ID NO:7:

(i) SEQUENCE CHARACTERISTICS:
        (A) LENGTH: 371 amino acids
        (B) TYPE: amino acid
        (D) TOPOLOGY: linear (xi) SEQUENCE DESCRIPTION: SEQ ID NO:7:

```
Val Thr Ala Ala Asp Thr Ala Val Tyr Tyr Cys Ala Arg Ala Thr
 1               5                  10                  15

Phe Cys Leu Trp Tyr Arg Glu Arg Pro Pro Cys Trp Ile Asp Pro
                20                  25                  30

Trp Gly Leu Gly Thr Leu Val Thr Val Ser Ser Ala Ser Thr Lys
                35                  40                  45

Gly Pro Ser Val Phe Pro Leu Ala Pro Ser Ser Lys Ser Thr Ser
                50                  55                  60

Gly Gly Thr Ala Ala Leu Gly Cys Leu Val Lys Asp Tyr Phe Pro
                65                  70                  75

Glu Pro Val Thr Val Ser Trp Asn Ser Gly Ala Leu Thr Ser Gly
                80                  85                  90

Val His Thr Phe Pro Ala Val Leu Gln Ser Ser Gly Leu Tyr Ser
                95                  100                 105

Leu Ser Ser Val Val Thr Val Pro Ser Ser Ser Leu Gly Thr Gln
                110                 115                 120

Thr Tyr Ile Cys Asn Val Asn His Lys Pro Ser Asn Thr Lys Val
                125                 130                 135

Asp Lys Lys Val Glu Pro Lys Ser Cys Asp Lys Thr His Thr Cys
                140                 145                 150

Pro Pro Cys Pro Ala Pro Glu Leu Leu Gly Gly Pro Ser Val Phe
```

```
                     155                 160                 165
Leu Phe Pro Pro Lys Pro Lys Asp Thr Leu Met Ile Ser Arg Thr
                170                 175                 180

Pro Glu Val Thr Cys Val Val Val Asp Val Ser His Glu Asp Pro
            185                 190                 195

Glu Val Lys Phe Asn Trp Tyr Val Asp Gly Val Glu Val His Asn
        200                 205                 210

Ala Lys Thr Lys Pro Arg Glu Glu Gln Tyr Asn Ser Thr Tyr Arg
    215                 220                 225

Val Val Ser Val Leu Thr Val Leu His Gln Asp Trp Leu Asn Gly
230                 235                 240

Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro
            260                 265                 270

Gln Val Tyr Thr Leu Pro Pro Ser Arg Asp Glu Leu Thr Lys Asn
        275                 280                 285

Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr
305                 310                 315

Lys Thr Thr Pro Pro Val Leu Asp Ser Asp Gly Ser Phe Phe Leu
                320                 325                 330

Tyr Ser Lys Leu Thr Val Asp Lys Ser Arg Trp Gln Gln Gly Asn
            335                 340                 345

Val Phe Ser Cys Ser Val Met His Glu Ala Leu His Asn His Tyr
        350                 355                 360

Thr Gln Lys Ser Leu Ser Leu Ser Pro Gly Lys
    365                 370 371

(2) INFORMATION FOR SEQ ID NO:8:

(i) SEQUENCE CHARACTERISTICS:
        (A) LENGTH: 1135 bases
        (B) TYPE: nucleic acid
        (C) STRANDEDNESS: single
        (D) TOPOLOGY: linear (xi) SEQUENCE DESCRIPTION: SEQ ID NO:8:

GAATTCTGTC ACTGCCGCGG ACACGGCCGT ATATTACTGT GCGAGAGCCA            50

CCTTTTGCCT ATGGTACAGG GAGCGTCCCC CTTGTTGGAT CGACCCCTGG           100

GGCCTGGGAA CCCTGGTCAC CGTCTCCTCG GCCTCCACCA AGGGCCCATC           150

GGTCTTCCCC CTGGCACCCT CCTCCAAGAG CACCTCTGGG GGCACAGCGG           200

CCCTGGGCTG CCTGGTCAAG GACTACTTCC CCGAACCGGT GACGGTGTCG           250

TGGAACTCAG GCGCCCTGAC CAGCGGCGTG CACACCTTCC CGGCTGTCCT           300

ACAGTCCTCA GGACTCTACT CCCTCAGCAG CGTGGTGACC GTGCCCTCCA           350

GCAGCTTGGG CACCCAGACC TACATCTGCA ACGTGAATCA CAAGCCCAGC           400

AACACCAAGG TGGACAAGAA AGTTGAGCCC AAATCTTGTG ACAAAACTCA           450

CACATGCCCA CCGTGCCCAG CACCTGAACT CCTGGGGGGA CCGTCAGTCT           500

TCCTCTTCCC CCCAAAACCC AAGGACACCC TCATGATCTC CCGGACCCCT           550

GAGGTCACAT GCGTGGTGGT GGACGTGAGC CACGAAGACC CTGAGGTCAA           600
```

-continued

| | |
|---|---|
| GTTCAAGTGG TACGTGGACG GCGTGGAGGT GCATAATGCC AAGACAAAGC | 650 |
| CGCGGGAGGA GCAGTACAAC AGCACGTACC GGGTGGTCAG CGTCCTCACC | 700 |
| GTCCTGCACC AGGACTGGCT GAATGGCAAG GAGTACAAGT GCAAGGTCTC | 750 |
| CAACAAAGCC CTCCCAGCCC CCATCGAGAA AACCATCTCC AAAGCCAAAG | 800 |
| GGCAGCCCCG AGAACCACAG GTGTACACCC TGCCCCCATC CCGGGATGAG | 850 |
| CTGACCAAGA ACCAGGTCAG CCTGACCTGC CTGGTCAAAG GCTTCTATCC | 900 |
| CAGCGACATC GCCGTGGAGT GGGAGAGCAA TGGGCAGCCG GAGAACAACT | 950 |
| ACAAGACCAC GCCTCCCGTG CTGGACTCCG ACGGCTCCTT CTTCCTCTAC | 1000 |
| AGCAAGCTCA CCGTGGACAA GAGCAGGTGG CAGCAGGGGA ACGTCTTCTC | 1050 |
| ATGCTCCGTG ATGCATGAGG CTCTGCACAA CCACTACACG CAGAAGAGCC | 1100 |
| TCTCCCTGTC TCCGGGTAAA TGAGTGCGAC GGCCG | 1135 |

(2) INFORMATION FOR SEQ ID NO:9:

(i) SEQUENCE CHARACTERISTICS:
        (A) LENGTH: 1142 bases
        (B) TYPE: nucleic acid
        (C) STRANDEDNESS: single
        (D) TOPOLOGY: linear (xi) SEQUENCE DESCRIPTION: SEQ ID NO:9:

| | |
|---|---|
| CTTAAGACAG TGACGGCGCC TGTGCCGGCA TATAATGACA CGCTCTCGGT | 50 |
| GGAAAACGGA TACCATGTCC CTCGCAGGGG GAACAACCTA GCTGGGGACC | 100 |
| CCGGACCCTT GGGACCAGTG GCAGAGGAGC CGGAGGTGGT TCCCGGGTAG | 150 |
| CCAGAAGGGG GACCGTGGGA GGAGGTTCTC GTGGAGACCC CCGTGTCGCC | 200 |
| GGGACCCGAC GGACCAGTTC CTGATGAAGG GGCTTGGCCA CTGCCACAGC | 250 |
| ACCTTGAGTC CGCGGGACTG GTCGCCGCAC GTGTGGAAGG GCCGACAGGA | 300 |
| TGTCAGGAGT CCTGAGATGA GGGAGTCGTC GCACCACTGG CACGGGAGGT | 350 |
| CGTCGAACCC GTGGGTCTGG ATGTAGACGT TGCACTTAGT GTTCGGGTCG | 400 |
| TTGTGGTTCC ACCTGTTCTT TCAACTCGGG TTTAGAACAC TGTTTTGAGT | 450 |
| GTGTACGGGT GGCACGGGTC GTGGACTTGA GGACCCCCCT GGCAGTCAGA | 500 |
| AGGAGAAGGG GGGTTTTGGG TTCCTGTGGG AGTACTAGAG GGCCTGGGGA | 550 |
| CTCCAGTGTA CGCACCACCA CCTGCACTCG GTGCTTCTGG GACTCCAGTT | 600 |
| CAAGTTGACC ATGCACCTGC CGCACCTCCA CGTATTACGG TTCTGTTTCG | 650 |
| GCGCCCTCCT CGTCATGTTG TCGTGCATGG CCCACCAGTC GCAGGAGTGG | 700 |
| CAGGACGTGG TCCTGACCGA CTTACCGTTC CTCATGTTCA CGTTCCAGAG | 750 |
| GTTGTTTCGG GAGGGTCGGG GGTAGCTCTT TTGGTAGAGG TTTCGGTTTC | 800 |
| CCGTCGGGGC TCTTGGTGTC CACATGTGGG ACGGGGTAG GGCCCTACTC | 850 |
| GACTGGTTCT TGGTCCAGTC GGACTGGACG GACCAGTTTC CGAAGATAGG | 900 |
| GTCGCTGTAG CGGCACCTCA CCCTCTCGTT ACCCGTCGGC CTCTTGTTGA | 950 |
| TGTTCTGGTG CGGAGGGCAC GACCTGAGGC TGCCGAGGAA GAAGGAGATG | 1000 |
| TCGTTCGAGT GGCACCTGTT CTCGTCCACC GTCGTCCCCT TGCAGAAGAG | 1050 |
| TACGAGGCAC TACGTACTAC GTACTCCGAG ACGTGTTGGT GATGTGCGTC | 1100 |
| TTCTCGGAGA GGGACAGAGG CCCATTTACT CACGCTGCCG GC | 1142 |

(2) INFORMATION FOR SEQ ID NO:10:

(i) SEQUENCE CHARACTERISTICS:
        (A) LENGTH: 143 amino acids
        (B) TYPE: amino acid
        (D) TOPOLOGY: linear (xi) SEQUENCE DESCRIPTION: SEQ ID NO:10:

Thr Leu Thr Ile Ser Gly Leu Gln Pro Glu Asp Phe Ala Thr Tyr
  1               5                  10                  15

Tyr Cys Gln Gln Tyr Lys Ser Leu Ser Leu Thr Phe Gly Gly Gly
                 20                  25                  30

Thr Lys Val Glu Ile Lys Arg Thr Val Ala Ala Pro Ser Val Phe
                 35                  40                  45

Ile Phe Pro Pro Ser Asp Glu Gln Leu Lys Ser Gly Thr Ala Ser
                 50                  55                  60

Val Val Cys Leu Leu Asn Asn Phe Tyr Pro Arg Glu Ala Leu Val
                 65                  70                  75

Gln Trp Leu Val Asp Asn Ala Leu Gln Ser Gly Asn Ser Gln Glu
                 80                  85                  90

Ser Val Thr Glu Gln Asp Ser Lys Asp Ser Thr Tyr Ser Leu Ser
                 95                 100                 105

Ser Thr Leu Thr Leu Ser Lys Ala Asp Tyr Glu Lys His Lys Val
                110                 115                 120

Tyr Ala Cys Glu Val Thr His Gln Gly Leu Ser Ser Pro Val Thr
                125                 130                 135

Lys Ser Phe Asn Arg Gly Glu Cys
                140         143

(2) INFORMATION FOR SEQ ID NO:11:

(i) SEQUENCE CHARACTERISTICS:
        (A) LENGTH: 468 bases
        (B) TYPE: nucleic acid
        (C) STRANDEDNESS: single
        (D) TOPOLOGY: linear (xi) SEQUENCE DESCRIPTION: SEQ ID NO:11:

GAATTCACTC TCACCATCAG CGGCCTGCAG CCTGAAGATT TTGCAACTTA         50

TTACTGCCAA CAGTATAAGA GTTTGTCGCT CACTTTCGGC GGAGGGACCA        100

AGGTGGAGAT CAAACGAACT GTGGCTGCAC CATCTGTCTT CATCTTCCCG        150

CCATCTGATG AGCAGTTGAA ATCTGGAACT GCCTCTGTTG TGTGCCTGCT        200

GAATAACTTC TATCCCAGAG AGGCCAAAGT ACAGTGGAAG GTGGATAACG        250

CCCTCCAATC GGGTAACTCC CAGGAGAGTG TCACAGAGCA GGACAGCAAG        300

GACAGCACCT ACAGCCTCAG CAGCACCCTG ACGCTGAGCA AAGCAGACTA        350

CGAGAAACAC AAAGTCTACG CCTGCGAAGT CACCCATCAG GGCCTGAGCT        400

CGCCCGTCAC AAAGAGCTTC AACAGGGGAG AGTGTTAGAG GGAGAAGTGC        450

CCCCACCTGC TCCTCAGT                                           468

(2) INFORMATION FOR SEQ ID NO:12:

(i) SEQUENCE CHARACTERISTICS:
        (A) LENGTH: 468 bases
        (B) TYPE: nucleic acid
        (C) STRANDEDNESS: single
        (D) TOPOLOGY: linear (xi) SEQUENCE DESCRIPTION: SEQ ID NO:12:

```
CTTAAGTGAG AGTGGTAGTC GCCGGACGTC GGACTTCTAA AACGTTGAAT          50

AATGACGGTT GTCATATTCT CAAACAGCGA GTGAAAGCCG CCTCCCTGGT         100

TCCACCTCTA GTTTGCTTGA CACCGACGTG GTAGACAGAA GTAGAAGGGC         150

GGTAGACTAC TCGTCAACTT TAGACCTTGA CGGAGACAAC ACACGGACGA         200

CTTATTGAAG ATAGGGTCTC TCCGGTTTCA TGTCACCTTC CACCTATTGC         250

GGGAGGTTAG CCCATTGAGG GTCCTCTCAC AGTGTCTCGT CCTGTCGTTC         300

CTGTCGTGGA TGTCGGAGTC GTCGTGGGAC TGCGACTCGT TTCGTCTGAT         350

GCTCTTTGTG TTTCAGATGC GGACGCTTCA GTGGGTAGTC CCGGACTCGA         400

GCGGGCAGTG TTTCTCGAAG TTGTCCCCTC TCACAATCTC CCTCTTCACG         450

GGGGTGGACG AGGAGTCA                                            468
```

(2) INFORMATION FOR SEQ ID NO:13:

(i) SEQUENCE CHARACTERISTICS:
        (A) LENGTH: 44 bases
        (B) TYPE: nucleic acid
        (C) STRANDEDNESS: single
        (D) TOPOLOGY: linear (xi) SEQUENCE DESCRIPTION: SEQ ID NO:13:

```
AATTCAAGCC CAGAGCCCTG CCATTTCTGT GGGCTCAGGT CCCT                 44
```

(2) INFORMATION FOR SEQ ID NO:14:

(i) SEQUENCE CHARACTERISTICS:
        (A) LENGTH: 50 bases
        (B) TYPE: nucleic acid
        (C) STRANDEDNESS: single
        (D) TOPOLOGY: linear (xi) SEQUENCE DESCRIPTION: SEQ ID NO:14:

```
ACTGCTCAGC CCCTTCCTCC CTCGGCAAGG CCACAATGAA CCGGGGAGTC           50
```

(2) INFORMATION FOR SEQ ID NO:15:

(i) SEQUENCE CHARACTERISTICS:
        (A) LENGTH: 47 bases
        (B) TYPE: nucleic acid
        (C) STRANDEDNESS: single
        (D) TOPOLOGY: linear (xi) SEQUENCE DESCRIPTION: SEQ ID NO:15:

```
CCTTTTAGGC ACTTGCTTCT GGTGCTGCAA CTGGCGCTCC TCCCAGC              47
```

(2) INFORMATION FOR SEQ ID NO:16:

(i) SEQUENCE CHARACTERISTICS:
        (A) LENGTH: 61 bases
        (B) TYPE: nucleic acid
        (C) STRANDEDNESS: single
        (D) TOPOLOGY: linear (xi) SEQUENCE DESCRIPTION: SEQ ID NO:16:

```
AGCCACTCAG GGAAACAAAG TGGTGCTGGG CAAAAAAGGG GATACAGTGG           50

AACTGACCTG T                                                    61
```

(2) INFORMATION FOR SEQ ID NO:17:

(i) SEQUENCE CHARACTERISTICS:
    (A) LENGTH: 51 bases
    (B) TYPE: nucleic acid
    (C) STRANDEDNESS: single
    (D) TOPOLOGY: linear (xi) SEQUENCE DESCRIPTION: SEQ ID NO:17:

ACAGGTCAGT TCCACTGTAT CCCCTTTTTT GCCCAGCACC ACTTTGTTTC         50

C                                                              51

(2) INFORMATION FOR SEQ ID NO:18:

(i) SEQUENCE CHARACTERISTICS:
    (A) LENGTH: 47 bases
    (B) TYPE: nucleic acid
    (C) STRANDEDNESS: single
    (D) TOPOLOGY: linear (xi) SEQUENCE DESCRIPTION: SEQ ID NO:18:

CTGAGTGGCT GCTGGGAGGA GCGCCAGTTG CAGCACCAGA AGCAAGT           47

(2) INFORMATION FOR SEQ ID NO:19:

(i) SEQUENCE CHARACTERISTICS:
    (A) LENGTH: 50 bases
    (B) TYPE: nucleic acid
    (C) STRANDEDNESS: single
    (D) TOPOLOGY: linear (xi) SEQUENCE DESCRIPTION: SEQ ID NO:19:

GCCTAAAAGG GACTCCCCGG TTCATTGTGG CCTTGCCGAG GGAGGAAGGG         50

(2) INFORMATION FOR SEQ ID NO:20:

(i) SEQUENCE CHARACTERISTICS:
    (A) LENGTH: 50 bases
    (B) TYPE: nucleic acid
    (C) STRANDEDNESS: single
    (D) TOPOLOGY: linear (xi) SEQUENCE DESCRIPTION: SEQ ID NO:20:

GCTGAGCAGT AGGGACCTGA GCCCACAGAA ATGGCAGGGC TCTGGGCTTG         50

(2) INFORMATION FOR SEQ ID NO:21:

(i) SEQUENCE CHARACTERISTICS:
    (A) LENGTH: 59 bases
    (B) TYPE: nucleic acid
    (C) STRANDEDNESS: single
    (D) TOPOLOGY: linear (xi) SEQUENCE DESCRIPTION: SEQ ID NO:21:

CTGCTCGAGC AGGGAAACAA AGTGGTGCTG GGCAAAAAAG GGGATACAGT         50

GGAACTGAC                                                      59

(2) INFORMATION FOR SEQ ID NO:22:

(i) SEQUENCE CHARACTERISTICS:
    (A) LENGTH: 59 bases
    (B) TYPE: nucleic acid
    (C) STRANDEDNESS: single
    (D) TOPOLOGY: linear (xi) SEQUENCE DESCRIPTION: SEQ ID NO:22:

ACAGGTCAGT TCCACTGTAT CCCCTTTTTT GCCCAGCACC ACTTTGTTTC         50

-continued

```
CCTGCTCGA                                                                59

(2) INFORMATION FOR SEQ ID NO:23:

(i) SEQUENCE CHARACTERISTICS:
        (A) LENGTH: 21 bases
        (B) TYPE: nucleic acid
        (C) STRANDEDNESS: single
        (D) TOPOLOGY: linear (xi) SEQUENCE DESCRIPTION: SEQ ID NO:23:

CGTGATAGAA GCTTTCTAGA G                                                  21

(2) INFORMATION FOR SEQ ID NO:24:

(i) SEQUENCE CHARACTERISTICS:
        (A) LENGTH: 51 bases
        (B) TYPE: nucleic acid
        (C) STRANDEDNESS: single
        (D) TOPOLOGY: linear (xi) SEQUENCE DESCRIPTION: SEQ ID NO:24:

CCCTTTTTTG CCCAGCACCA CCTTCTTGCC CTGAGTGGCT GCTGGGAGGA                   50

G                                                                        51

(2) INFORMATION FOR SEQ ID NO:25:

(i) SEQUENCE CHARACTERISTICS:
        (A) LENGTH: 16 bases
        (B) TYPE: nucleic acid
        (C) STRANDEDNESS: single
        (D) TOPOLOGY: linear (xi) SEQUENCE DESCRIPTION: SEQ ID NO:25:

CCACCTTCTT GCCCTG                                                        16
```